US009737892B2

(12) United States Patent
Mellem et al.

(10) Patent No.: US 9,737,892 B2
(45) Date of Patent: Aug. 22, 2017

(54) DEVICE FOR SIMULTANEOUS AND UNIFORM THERMAL CYCLING OF SAMPLES AND USES THEREOF

(71) Applicant: Curiosity Diagnostics sp. z o.o., Warsaw (PL)

(72) Inventors: Krzysztof Mellem, Jelenia Gora (PL); Daniel Krzystof Gorzkowski, Kozienice (PL); Seweryn Bajer-Borstyn, Warsaw (PL); Pawel Zawadzki, Sokolow Podlaski (PL); Piotr Garstecki, Warsaw (PL); Kamil Robert Gewartowski, Warsaw (PL)

(73) Assignee: Curiosity Diagnostics sp. z o.o., Warsaw (PL)

( * ) Notice: Subject to any disclaimer, the term of this patent is extended or adjusted under 35 U.S.C. 154(b) by 0 days.

(21) Appl. No.: 15/048,731

(22) Filed: Feb. 19, 2016

(65) Prior Publication Data

US 2016/0167054 A1 Jun. 16, 2016

Related U.S. Application Data

(63) Continuation of application No. PCT/EP2015/056454, filed on Mar. 25, 2015.

(30) Foreign Application Priority Data

Mar. 28, 2014 (EP) ..................... 14162212

(51) Int. Cl.
*C12Q 1/68* (2006.01)
*B01L 7/00* (2006.01)

(52) U.S. Cl.
CPC ................ *B01L 7/52* (2013.01); *C12Q 1/686* (2013.01); *B01L 2300/0654* (2013.01);
(Continued)

(58) Field of Classification Search
None
See application file for complete search history.

(56) References Cited

U.S. PATENT DOCUMENTS 8,507,257 B2  8/2013  Dale et al.
2002/0047003 A1  4/2002  Bedingham et al.
(Continued)

FOREIGN PATENT DOCUMENTS

WO    2013/100859 A1    7/2013

OTHER PUBLICATIONS

Kim, Hanyoup et al., "Nanodroplet real-time PCR system with laser assisted heating", Molecular Physics Laboratory and Biosciences Division, SRI International, Menlo Park, CA, Optical Society of America; Optics Express, vol. 17, Issue 1, Jan. 5, 2009, pp. 218-227.

*Primary Examiner* — Betty Forman
(74) *Attorney, Agent, or Firm* — Michael A. Glenn; Perkins Coie LLP

(57) ABSTRACT

The invention relates to thermal cycling device comprising: a sample location; a first heating means, wherein advantageously said first heating means is a contact heating means; a second heating means, wherein said second heating means is configured to bring said sample to a second temperature by directing electromagnetic radiation to the first light pipe section end and the light pipe section is configured to direct said electromagnetic radiation through its second end to the sample location, its uses and methods based thereon.

28 Claims, 11 Drawing Sheets

(52) U.S. Cl.
CPC .. *B01L 2300/168* (2013.01); *B01L 2300/1811* (2013.01); *B01L 2300/1827* (2013.01); *B01L 2300/1872* (2013.01)

(56) References Cited

U.S. PATENT DOCUMENTS

| | | | |
|---|---|---|---|
| 2005/0287661 A1 | 12/2005 | Landers | |
| 2008/0176230 A1* | 7/2008 | Owen | B01L 7/52 435/6.11 |
| 2014/0045250 A1* | 2/2014 | Kreifels | C12Q 1/686 435/287.2 |

* cited by examiner

DEVICE FOR SIMULTANEOUS AND UNIFORM THERMAL CYCLING OF SAMPLES AND USES THEREOF

CROSS-REFERENCE TO RELATED APPLICATIONS

This application is a continuation of copending International Application No. PCT/EP2015/056454, filed Mar. 25, 2015, which claims priority from European Application No. EP 14162212.6, filed Mar. 28, 2014, which are each incorporated herein in its entirety by this reference thereto.

BACKGROUND OF THE INVENTION

The present invention relates to the field of thermal cycling devices, their uses and methods based thereon. The present invention in particular relates to a thermal cycling device comprising: a sample location; a first heating means, wherein said first heating means is configured to bring a sample at said sample location to at least about a first temperature; advantageously said first heating means is a contact heating means; a second heating means, wherein said second heating means is configured to bring said sample to a second temperature by directing electromagnetic radiation to the first light pipe section end and the light pipe section is configured to direct said electromagnetic radiation through its second end to the sample location. According to the present invention a light pipe (or a light pipe section) is used to homogenize spatial intensity distribution of heating electromagnetic radiation and to illuminate said sample at said sample location with light during thermal cycling. The present invention also relates to uses of the thermal cycler and light pipe of the present invention and to an ultra-fast PCR amplification methods based thereon. The invention also relates to a thermal cycling device comprising: a) a sample location (4); b) a first light pipe section at least operable to collect electromagnetic radiation; c) a second light pipe section at least operable to collect fluorescent excitation and transmit fluorescence emission light; d) a third light pipe section at least operable to illuminate the sample location (4) with electromagnetic radiation and fluorescent excitation and to transmit fluorescent emission light to the second light pipe section; e) an optical filter configured to reflect visible light and transmit electromagnetic radiation; wherein each light pipe section is configured to homogenize spatial intensity distribution of light and electromagnetic radiation by the means of reflection; its uses and methods based thereon.

BACKGROUND OF INVENTION

The present invention relates to complex thermal cycling devices comprising electromagnetic radiation-based heating means combined with other heating means (e.g. contact heating means) and a light pipe section (or a light pipe) for uniform and simultaneous temperature cycling of samples (or multiple samples, e.g. multiple PCR samples) that allow uniform (e.g. at least 90%, advantageously at least 95%, more advantageously at least 98%), simultaneous and ultra-fast (e.g. up to 3.7 seconds, e.g. up to 7 seconds, e.g. in the range between 3 and 7 seconds) thermal cycling across samples (or across multiple samples, e.g. multiple PCR samples) at sample location.

PCR (or polymerase chain reaction) is a method for amplification of nucleic acids or fragments thereof. PCR is a diagnostic technique that is used routinely to detect target DNA, for example in diagnosis of an infectious disease, oncology or forensics. In many cases it is beneficial to get test result as quickly as possible, for instance to prescribe proper medicine during visit to doctor's office. In order to amplify target DNA a PCR reaction necessitates cyclic changes of sample temperature.

PCR amplification typically comprises three stages: denaturation, annealing of primers and extension, which together make a PCR cycle. PCR cycles can be repeated until a desired amount of the product is amplified. Typical PCR cycle lasts about one minute. The most advanced PCR thermal cyclers are able to perform a PCR cycle in about 20 seconds.

For this reason to lower test time it is crucial to provide a method for fast heating of the sample (e.g. multiple samples). The conventional technology achieves this goal by the means of infrared radiation, a contactless heating method that allows for direct, fast heating of sample especially if the sample volume is low. In order to provide accurate diagnosis it is crucial to test for as many potential pathogenic organisms as possible, to eliminate false negative results, which necessitates large number of PCR reactions to be thermally cycled uniformly and simultaneously. Accordingly, the present invention provides means to homogenize spatial intensity distribution of electromagnetic radiation which substantially improves thermal cycle profile uniformity within the tested samples. Ultrafast thermal cycling of multiple nucleic acid samples by infrared heating necessitates substantial amount of power. Furthermore, Real-Time PCR also demands high power of fluorescence excitation light in order to achieve high detection sensitivity. Losses of electromagnetic light would result either in slower heating of samples or defects in detection and may result in unwanted heating of the thermal cycler. The present invention addresses this problem in two ways: firstly, by providing efficient way of collecting and transmitting electromagnetic radiation and fluorescence excitation to the sample (e.g. multiple samples) and secondly by providing means for effective cooling of parts of the thermal cycler that were heated by the remaining losses of radiated energy.

The use of the present invention provides uniform, simultaneous and ultra-fast (e.g. up to 3.7 seconds, e.g. up to 7 seconds, e.g. in the range between 3 and 7 seconds) PCR cycles across multiple samples (e.g. multiple PCR samples). It is contemplated in the present invention that by increasing the power of the radiation it is possible to reach the limit of polymerization speed of polymerase used in a PCR reaction (e.g. DNA polymerase), which translates into approximately 1 second PCR cycle. While the use of electromagnetic radiation for heating is known in conventional technology (Kim H., Dixit S., Green C J., Faris G W., 2009, Optics Express, Vol. 17, No. 1), none of the conventional devices provide uniform, simultaneous and ultra-fast thermal cycling across multiple samples (e.g. multiple PCR samples).

The conventional technology also teaches to expedite cooling of sample enclosed in a microfluidic chip by the means of Peltier element. However, control over temperature of the thermal block is not sufficient to accurately change sample temperature during thermal cycling.

Accordingly, there is a need in conventional technology for means and methods that would allow uniform, simultaneous and ultra-fast thermal cycling across samples (or multiple samples, e.g. multiple PCR samples).

For the purposes of the present invention, all references as cited herein are incorporated by reference in their entireties.

SUMMARY

According to an embodiment, a thermal cycling device may have: a sample location; a light source; a light pipe having a light pipe section, the light pipe section having a first and a second end; a first heating means being a contact heat source, wherein said first heating means is configured to bring a sample at said sample location to at least about a first temperature; a second heating means being a source of electromagnetic radiation, wherein said second heating means is configured to simultaneously bring multiple samples at said sample location to a second temperature by directing the electromagnetic radiation to the first light pipe section end and the light pipe section is configured to direct said electromagnetic radiation through its second end to the sample location and homogenize a spatial intensity distribution of the electromagnetic radiation by the means of reflection; and a camera (configured to directly observe emitted fluorescence from the sample location transmitted by the light pipe section without reflections from sides of the light pipe.

Another embodiment may have the use of the inventive thermal cycling device, for uniform and simultaneous thermal cycling of samples, advantageously for uniform, simultaneous and ultra-fast thermal cycling of samples.

Another embodiment may have the use of the inventive device, further having at least one fluorescence filter, wherein said fluorescence filter is a multiband fluorescence filter, wherein said fluorescence filter is configured to measure fluorescence intensity changes of a temperature sensitive dye added to sample, advantageously said temperature sensitive dye is Rhodamine B, more advantageously said fluorescence filter is a multiband filter, for measuring temperature of the samples in real time.

According to another embodiment, a method for performing thermal cycling using a thermal cycling device having a sample location; a light source; a light pipe having a light pipe section, the light pipe section having a first and a second end; a heating means being a source of electromagnetic radiation, wherein said heating means is configured to simultaneously bring multiple samples at said sample location to a temperature by directing the electromagnetic radiation to the first light pipe section end and the light pipe section is configured to direct said electromagnetic radiation through its second end to the sample location and homogenize a spatial intensity distribution of the electromagnetic radiation by the means of reflection; and a camera configured to directly observe emitted fluorescence from the sample location transmitted by the light pipe section without reflections from sides of the light pipe, may have the steps of: directing of said electromagnetic radiation to sample location using the heating means and using the homogenization of the spatial intensity distribution of electromagnetic radiation; illuminating said sample location with light during thermal cycling using the light source; and performing real-time fluorescence detection using the camera.

According to another embodiment, a method for uniform and simultaneous amplification of samples with PCR using a thermal cycling device having a sample location; a light source; a light pipe having a light pipe section, the light pipe section having a first and a second end; a first heating means being a contact heat source, wherein said first heating means is configured to bring a sample at said sample location to at least about a first temperature; a second heating means being a source of electromagnetic radiation, wherein said second heating means is configured to simultaneously bring multiple samples at said sample location to a second temperature by directing the electromagnetic radiation to the first light pipe section end and the light pipe section is configured to direct said electromagnetic radiation through its second end to the sample location and homogenize a spatial intensity distribution of the electromagnetic radiation by the means of reflection; and a camera configured to directly observe emitted fluorescence from the sample location transmitted by the light pipe section without reflections from sides of the light pipe, said samples having a nucleic acid or a fragment thereof, combined with realtime detection of amplified product, may have the steps of: (a) maintaining the temperature of the first heating means at a specific temperature, wherein said specific temperature is below or equal to the temperature of the annealing of the PCR primers; (b) while maintaining said temperature constant, turning on a source of electromagnetic radiation at a constant power for a specified period of time, wherein uniformly and simultaneously heating said samples until they reach the temperature of DNA denaturation; (c) while still maintaining the temperature of the first heating means, turning off the source of electromagnetic radiation for a specified period of time, wherein cooling said samples; advantageously repeating steps (b)-(c) at least 15 times, more advantageously repeating steps (b)-(c) at least 20 times, most advantageously repeating steps (b)-(c) at least 30 times; further advantageously repeating steps (b)-(c) at least 40 times; (d) after specified period of time turning on the source of fluorescence excitation, wherein uniformly and simultaneously exciting said samples, and simultaneously performing detection of emitted fluorescence light using the camera.

According to another embodiment, a method for controlling temperature of samples in the inventive device, further having at least one fluorescence filter, wherein said fluorescence filter is a multiband fluorescence filter, wherein said fluorescence filter is configured to measure fluorescence intensity changes of a temperature sensitive dye added to sample, advantageously said temperature sensitive dye is Rhodamine B, more advantageously said fluorescence filter is a multiband filter, in real time during thermal cycling, may have the steps of: keeping the source of fluorescence excitation on or turning it on periodically, while simultaneously reading fluorescence excitation changes caused by change of temperature using the camera during thermal cycling.

According to another embodiment, a thermal cycling device may have: a) a sample location; b) a first light pipe section at least operable to collect electromagnetic radiation; c) a second light pipe section at least operable to collect fluorescent excitation and transmit fluorescence emission light; d) a third light pipe section at least operable to illuminate said sample location with electromagnetic radiation and fluorescent excitation and to transmit fluorescent emission light to the second light pipe section; e) an optical filter configured to reflect visible light and transmit electromagnetic radiation; wherein each light pipe section is configured to homogenize spatial intensity distribution of light and electromagnetic radiation by the means of reflection.

The present invention provides a thermal cycling device comprising: a) a sample location (4); b) a first heating means (3), wherein said first heating means is configured to bring a sample at said sample location to at least about a first temperature; advantageously said first heating means is a contact heating means; c) a second heating means (2), wherein said second heating means is configured to bring said sample to a second temperature by directing electromagnetic radiation to the first light pipe section end and the light pipe section is configured to direct said electromagnetic radiation through its second end to the sample location (4). In another embodiment the invention provides a thermal cycling device comprising: a) a sample location (4); b) a light pipe section comprising a first and a second end, wherein said light pipe section is configured to homogenize spatial intensity distribution of electromagnetic radiation by the means of reflection, advantageously inner surfaces of said light pipe section are reflective; c) a first heating means (3), wherein said first heating means is configured to bring a sample at said sample location to at least about a first temperature; advantageously said first heating means is a contact heating means; d) a second heating means (2), wherein said second heating means is configured to simultaneously bring multiple samples at said sample location to a second temperature by directing electromagnetic radiation to the first light pipe section end and the light pipe section is configured to direct said electromagnetic radiation through its second end to the sample location (4). In one embodiment the invention provides the thermal cycling device, wherein said electromagnetic radiation directed to said sample location (4) causes at least 5° C. temperature increase of said sample; advantageously at least 10° C. temperature increase of said sample; more advantageously at least 15° C. temperature increase of said sample; most advantageously at least 20° C. temperature increase of said sample. In another embodiment the invention provides the thermal cycling device, wherein said electromagnetic radiation directed to said sample location (4) is configured to simultaneously cause at least 5° C. temperature increase of said multiple samples; advantageously at least 10° C. temperature increase of said multiple samples; more advantageously at least 15° C. temperature increase of said multiple samples; most advantageously at least 20° C. temperature increase of said multiple samples. In another embodiment the invention provides the thermal cycling device, wherein said light pipe section is configured to homogenize spatial intensity distribution of said electromagnetic radiation. In another embodiment the invention provides the thermal cycling device, wherein said light pipe section is configured to homogenize spatial intensity distribution of said electromagnetic radiation by the means of reflection. In another embodiment the invention provides the thermal cycling device, wherein: a) said second heating means (2) is a source of electromagnetic radiation; advantageously a source of infrared electromagnetic radiation; b) said first heating means (3) is a contact heat source; c) a light pipe (1) comprises said light pipe section, wherein said light pipe is configured to homogenize spatial intensity distribution of the heating electromagnetic radiation; advantageously said light pipe is a hollow light pipe or a solid glass pipe. In another embodiment the invention provides the thermal cycling device, wherein said light pipe is configured to illuminate said sample at said sample location (4) with light during thermal cycling. In another embodiment the invention provides the thermal cycling device, wherein said light pipe is configured to simultaneously illuminate said multiple samples at said sample location (4) with light during thermal cycling by the means of reflection. In another embodiment the invention provides the thermal cycling device, wherein said pipe comprises a chamber that has a reflective surface on one side and a semi-reflective surface on the other side, advantageously said chamber is within said light pipe (1). In another embodiment the invention provides the thermal cycling device, wherein said pipe has a cross-section selected from the group consisting of: rectangular, square and hexagonal cross-section. In another embodiment the invention provides the thermal cycling device, wherein uniformity of electromagnetic energy distribution from second heating means (2) to samples at sample location (4) is at least 90%, advantageously at least 95%, more advantageously at least 98%. In another embodiment the invention provides the thermal cycling device, wherein uniformity of electromagnetic energy distribution from second heating means (2) to said multiple samples at sample location (4) is at least 90%, advantageously at least 95%, more advantageously at least 98%. In another embodiment the invention provides the thermal cycling device, wherein said device further comprises: d) light source (5), advantageously said light source is a source of fluorescence excitation, e) at least one dichroic mirror (6), advantageously a set of dichroic mirrors (6, 7), more advantageously the dichroic mirror (6) is a multiband fluorescence dichroic mirror, f) camera (8), advantageously said camera is an emitted fluorescence light detection camera, g) at least one fluorescence filter (9), advantageously said fluorescence filter is an emission filter, more advantageously multiple fluorescence filters, most advantageously said at least one fluorescence filter is a multiband fluorescence filter, h) optionally an additional filter (10), wherein said additional filter reflects wavelengths below infrared. In another embodiment the invention provides the thermal cycling device, wherein fluorescence filter (9) is configured to measure fluorescence intensity changes of a temperature sensitive dye added to sample, advantageously said temperature sensitive dye is Rhodamine B, more advantageously said fluorescence filter is a multiband filter. In another embodiment the invention provides a use of the thermal cycling device of the present invention for uniform (e.g. at least 90%, advantageously at least 95%, more advantageously at least 98%) and simultaneous thermal cycling of samples, advantageously for uniform, simultaneous and ultra-fast (PCR cycle—e.g. up to 3.7 seconds, e.g. up to 7 seconds, e.g. in the range between 3 and 7 seconds) thermal cycling of samples (e.g. multiple PCR samples). In another embodiment the invention provides a use of the device of the present invention for measuring temperature of the samples in real time. In another embodiment the invention provides a use of the light pipe (1) in a thermal cycling device, said use comprising: a) homogenization of spatial intensity distribution of electromagnetic radiation from a source of electromagnetic radiation (2); and b) directing of said electromagnetic radiation to sample location (4); and c) illumination of said sample at said sample location with light during thermal cycling; and d) optionally, said illumination is combined with real-time fluorescence detection, advantageously real-time fluorescence detection of amplified PCR products. In another embodiment the invention provides a use of the light pipe (1) in a thermal cycling device, wherein said thermal cycling device comprises said light pipe (1), said use comprising: a) homogenization of spatial intensity distribution of electromagnetic radiation from a source of electromagnetic radiation (2) by the means of reflection; and b) directing of said electromagnetic radiation to sample location (4); and c) illumination of said sample at said sample location with light during thermal cycling; and d) optionally, said illumination is combined with real-time fluorescence detection, advantageously real-time fluorescence detection of amplified PCR products. In another embodiment the invention provides a method for uniform and simultaneous amplification of samples with PCR, advantageously said method is carried out in the device of the present invention, said samples comprising a nucleic acid or a fragment thereof, combined with real-time detection of amplified product, said method comprising: (a) maintaining the temperature of the first heating means (3) at a specific temperature, wherein said specific temperature is below or equal to the temperature of the annealing of the PCR primers; (b) while maintaining said temperature constant, turning on the source of electromagnetic radiation (2) at a constant power for a specified period of time, wherein uniformly and simultaneously heating said samples until they reach the temperature of DNA denaturation; (c) while still maintaining the temperature of the first heating means (3), turning off the source of electromagnetic radiation (2) for a specified period of time, wherein cooling said samples; advantageously repeating steps (b)-(c) at least 15 times, more advantageously repeating steps (b)-(c) at least 20 times, most advantageously repeating steps (b)-(c) at least 30 times; further advantageously repeating steps (b)-(c) at least 40 times; (d) after specified period of time turning on the source of fluorescence excitation (5), wherein uniformly and simultaneously exciting said samples, and simultaneously performing detection of emitted fluorescence light using the camera (8). In another embodiment the invention provides a method for controlling temperature of samples in a device of the present invention in real time during thermal cycling, said method comprising: keeping the source of fluorescence excitation (5) on or turning it on periodically, while simultaneously reading fluorescence excitation changes caused by change of temperature using the camera (8) during thermal cycling. In another embodiment the present invention provides a thermal cycling device, wherein said first heating means (3) is an electrical heat source; advantageously said first heating means (3) is a thermal block or thermal chamber, more advantageously said thermal block comprises a plurality of heating elements. In another embodiment the invention provides a thermal cycling device, wherein said device comprises only one light pipe (1) or multiple light pipes, wherein each of said multiple light pipes is connected to a separate source of electromagnetic radiation, wherein each of said multiple light pipes is also connected to a larger light pipe that is configured: a) to homogenize spatial intensity distribution of electromagnetic radiation; b) to direct said electromagnetic radiation to sample location (4); c) to illuminate said sample at said sample location (4) with light during thermal cycling. In another embodiment of the invention the device of the present invention is a PCR thermal cycler. In another embodiment of the invention the device of the present invention is used for PCR thermal cycling of samples.

In another embodiment the invention provides a thermal cycling device for uniform (e.g. at least 90%, advantageously at least 95%, more advantageously at least 98%) and simultaneous thermal cycling of samples comprising: a) light pipe (1); advantageously a hollow light pipe; that is configured to uniformly (e.g. at least 90%, advantageously at least 95%, more advantageously at least 98%) and simultaneously distribute electromagnetic energy from an electromagnetic heat source to samples and to uniformly and simultaneously illuminate said samples with light during said thermal cycling, b) electromagnetic heat source, wherein said electromagnetic heat source is a source of electromagnetic radiation (2), advantageously a source of infrared electromagnetic radiation, c) a first heating means (3), wherein said first heating means (3) is a contact heat source, d) sample location (4) (e.g. sample container or sample holder). In another embodiment of the invention light pipe (1) is a hollow light pipe. In the present invention the term "uniformly" has the meaning of having at least 90% of uniformity, advantageously at least 95% of uniformity, more advantageously at least 98% of uniformity. In the present invention the term "sample location" (4) can e.g. be a sample container or sample holder. In another embodiment the invention provides a thermal cycling device for uniform and simultaneous thermal cycling of samples comprising: a) light pipe (1), wherein inner surfaces of said light pipe are reflective and the volume enclosed by said pipe is transmissive, wherein said light pipe (1) is configured to uniformly and simultaneously distribute electromagnetic energy from an electromagnetic heat source to samples and to uniformly and simultaneously illuminate said samples with light during said thermal cycling, (advantageously hollow light pipe), b) electromagnetic heat source, wherein said electromagnetic heat source is a source of electromagnetic radiation (2), advantageously a source of infrared electromagnetic radiation, c) a first heating means (3), wherein said first heating means (3) is a contact heat source, d) sample location (4) (e.g. sample container or sample holder). In one embodiment of the invention a first heating means (3) is a contact heat source. In another embodiment of the invention a first heating means (3) is an electrical heat source, advantageously said first heating means (3) is a thermal block or thermal chamber. In another embodiment of the invention the device of the present invention comprises only one light pipe (1). In another embodiment of the invention the light pipe (1) comprises a chamber that has a reflective surface on one side and a semi-reflective surface on the other side. In still another embodiment of the invention the light pipe (1) has a cross-section selected from the group consisting of: rectangular, square and hexagonal cross-section. In another embodiment of the invention the light pipe (1) has a width to length ratio of approximately 1 (e.g. equals 1), advantageously said width to length ratio is bigger than 3, more advantageously said width to length ratio is bigger than 5. In another embodiment of the invention the uniformity of electromagnetic energy distribution from electromagnetic heat source, wherein said electromagnetic heat source is a source of electromagnetic radiation (2) to samples at sample location is at least 90%, advantageously at least 95%, more advantageously at least 98%. In another embodiment of the invention the device of the present invention further comprises: d) light source (5), advantageously said light source is a source of fluorescence excitation, e) at least one dichroic mirror (7), advantageously a set of dichroic mirrors (6, 7), more advantageously the dichroic mirror (6) is a multiband fluorescence dichroic mirror, f) camera (8), advantageously said camera is an emitted fluorescence light detection camera, g) at least one fluorescence filter (9), advantageously said fluorescence filter is an emission filter, more advantageously multiple fluorescence filters, most advantageously said at least one fluorescence filter is a multiband fluorescence filter, h) optionally an additional filter (10), wherein said additional filter reflects wavelengths below infrared. In further embodiment of the invention the thermal cycling of samples is a PCR thermal cycling of samples. In another embodiment of the invention thermal cycling device for uniform and simultaneous thermal cycling of samples is the PCR thermal cycling device for uniform and simultaneous thermal cycling of samples. In another embodiment of the invention PCR thermal cycling device for uniform and simultaneous thermal cycling of samples is the PCR thermal cycling device for uniform and simultaneous thermal cycling of PCR samples. In another embodiment of the invention a thermal cycling device of the present invention is a PCR thermal cycling device. In another embodiment of the invention a thermal cycling device of the present invention is used for PCR thermal cycling. In another embodiment of the invention light source (5) is configured to be a source of fluorescence excitation. In another embodiment of the invention camera (8) is configured to detect emitted fluorescence light. In another embodiment of the invention the thermal cycling device of the present invention is used for uniform and simultaneous thermal cycling of samples. In another embodiment of the invention the thermal cycling device is used for uniform and simultaneous thermal cycling of PCR samples. In another embodiment of the invention the thermal cycling device of the present invention is used for uniform, simultaneous and ultra-fast (e.g. with a PCR cycle e.g. up to 3.7 seconds, e.g. up to 7 seconds, e.g. in the range between 3 and 7 seconds) thermal cycling of PCR samples. In another embodiment of the invention light pipe (1) is used for uniformly and simultaneously distributing electromagnetic energy from electromagnetic heat source to samples during thermal cycling in a thermal cycling device. In another embodiment of the invention light pipe (1) is used for uniformly and simultaneously distributing electromagnetic energy from electromagnetic heat source to samples during PCR thermal cycling in a thermal cycling device. In another embodiment of the invention light pipe (1) is used for uniformly and simultaneously distributing electromagnetic energy from electromagnetic heat source to samples during PCR thermal cycling in a PCR thermal cycling device. In another embodiment of the invention light pipe (1) is used for uniformly and simultaneously distributing electromagnetic energy from electromagnetic heat source to samples during thermal cycling in a PCR thermal cycling device. In another embodiment of the invention light pipe (1) is used for uniformly and simultaneously distributing electromagnetic energy from electromagnetic heat source to PCR samples during PCR thermal cycling in a PCR thermal cycling device. In further embodiment of the invention thermal cycling is the PCR thermal cycling. In another embodiment of the invention thermal cycling device is the PCR thermal cycling device. In further embodiment of the invention samples (or sample) are PCR samples (or PCR sample) (e.g. PCR reaction mixtures or PCR reaction mixture). In another embodiment of the invention light pipe (1) is used for uniformly and simultaneously distributing electromagnetic energy from electromagnetic heat source to samples during thermal cycling in a thermal cycling device and for uniformly and simultaneously illuminating said samples with light during said thermal cycling. In another embodiment of the invention light pipe (1) is used for uniformly and simultaneously distributing electromagnetic energy from electromagnetic heat source to samples during thermal cycling in a thermal cycling device and for uniformly and simultaneously illuminating said samples with light during said thermal cycling, wherein said illumination is combined with real-time fluorescence detection, advantageously real-time fluorescence detection of amplified PCR products. In another embodiment of the invention light pipe (1), wherein inner surfaces of said light pipe are reflective and the volume enclosed by said pipe is transmissive, is used for uniformly and simultaneously distributing electromagnetic energy from electromagnetic heat source to samples during thermal cycling in a thermal cycling device and for uniformly and simultaneously illuminating said samples with light during said thermal cycling, wherein said illumination is combined with real-time fluorescence detection, advantageously real-time fluorescence detection of amplified PCR products. The invention also provides a method for uniform and simultaneous amplification of samples with PCR, said samples comprising a nucleic acid or a fragment thereof, combined with real-time detection of amplified product, said method comprising: (a) maintaining the temperature of the first heating means (3) at a specific temperature, wherein said specific temperature is below or equal to the temperature of the annealing of the PCR primers; (b) while maintaining said temperature constant, turning on the source of electromagnetic radiation (2) at a constant power for a specified period of time, wherein uniformly and simultaneously heating said samples until they reach the temperature of DNA denaturation; (c) while still maintaining the temperature of the first heating means (3), turning off the source of electromagnetic radiation (2) for a specified period of time, wherein cooling said samples; advantageously repeating steps (b)-(c) at least 15 times, more advantageously repeating steps (b)-(c) at least 20 times, most advantageously repeating steps (b)-(c) at least 30 times; further advantageously repeating steps (b)-(c) at least 40 times; (d) after specified period of time turning on the source of fluorescence excitation, wherein uniformly and simultaneously exciting said samples, and simultaneously performing detection of emitted fluorescence light using the camera (8). In another embodiment of the invention provides a method for uniform and simultaneous amplification of samples with PCR, said samples comprising a nucleic acid or a fragment thereof, combined with real-time detection of amplified product, said method comprising: (a) maintaining the temperature of the a first heating means (3) at a specific temperature, wherein said specific temperature is below or equal to the temperature of the annealing of the PCR primers; (b) while maintaining said temperature constant, turning on the source of electromagnetic radiation (2) at a constant power for a specified period of time, wherein uniformly and simultaneously heating said samples through light pipe (1) until they reach the temperature of DNA denaturation; (c) while still maintaining the temperature of the first heating means (3), turning off the source of electromagnetic radiation (2) for a specified period of time, wherein cooling said samples; advantageously repeating steps (b)-(c) at least 15 times, more advantageously repeating steps (b)-(c) at least 20 times, most advantageously repeating steps (b)-(c) at least 30 times; further advantageously repeating steps (b)-(c) at least 40 times; (d) after specified period of time turning on the source of fluorescence excitation, wherein uniformly and simultaneously exciting said samples, and simultaneously performing detection of emitted fluorescence light using the camera (8). In another embodiment of the invention a method of the present invention is carried out in a thermal cycling device of the present invention. In another embodiment of the invention the thermal cycling device of the present invention is used in a PCR method of the present invention.

In another embodiment the present invention provides a thermal cycling device comprising: a) a sample location (4); b) a first light pipe section at least operable to collect electromagnetic radiation; c) a second light pipe section at least operable to collect fluorescent excitation and transmit fluorescence emission light; d) a third light pipe section at least operable to illuminate said sample location (4) with electromagnetic radiation and fluorescent excitation and to transmit fluorescent emission light to the second light pipe section; e) an optical filter configured to reflect visible light and transmit electromagnetic radiation; wherein each light pipe section is configured to homogenize spatial intensity distribution of light and electromagnetic radiation by the means of reflection.

In another embodiment the present invention provides a thermal cycling device comprising: a) a sample location (4);

b) a first light pipe section at least operable to collect electromagnetic radiation; c) a second light pipe section at least operable to collect fluorescent excitation and transmit fluorescence emission light, advantageously said second light pipe section is configured to homogenize the fluorescent excitation intensity; d) a third light pipe section at least operable to illuminate said sample location (4) with electromagnetic radiation and fluorescent excitation and to transmit fluorescent emission light to the second light pipe section, wherein said third light pipe section is configured to homogenize the fluorescent excitation intensity; e) an optical filter configured to reflect visible light and transmit electromagnetic radiation; wherein at least one light pipe section is configured to homogenize spatial intensity distribution of light and electromagnetic radiation by the means of reflection.

In another embodiment the present invention a fluorescent excitation intensity is homogenized by a third light pipe section, wherein a second light pipe section is only advantageously configured to homogenize said intensity of fluorescent excitation.

In another embodiment the present invention provides the thermal cycling device of the present invention further comprising a light pipe (1), wherein said light pipe (1) comprises said first, second and third light pipe sections. In another embodiment the present invention provides the thermal cycling device of the present invention, further comprising: a first heating means (3); a second heating means (2), wherein said second heating means (2) is a source of electromagnetic radiation; a light source (5); and a camera (8). In another embodiment the present invention provides the thermal cycling device of the present invention, wherein: a) said first light pipe section is at least operable to collect electromagnetic radiation from said second heating means (2); b) said second light pipe section is at least operable to collect fluorescent excitation from said light source (5) and transmit a fluorescence emission light from said third light pipe section to said camera (8); c) said third light pipe section is at least operable to illuminate said sample location (4) with said electromagnetic radiation and said fluorescent excitation and to transmit said fluorescent emission light from said sample location (4) to said second light pipe section. In another embodiment the present invention provides the thermal cycling device of the present invention, wherein said first heating means (3) is a contact heating means. In another embodiment the present invention provides the thermal cycling device of the present invention, wherein at least one of said first, second or third light pipe sections is made of metal. In another embodiment the present invention provides the thermal cycling device of the present invention, wherein said light pipe (1) is made of metal. In another embodiment the present invention provides the thermal cycling device of the present invention, wherein said third light pipe section or said light pipe (1) is configured to press said sample location (4) to said contact heating means (3). In another embodiment the present invention provides the thermal cycling device of the present invention, wherein said light pipe (1) is configured to press said sample location (4) to said contact heating means (3). In another embodiment the present invention provides the thermal cycling device of the present invention, wherein at least said third light pipe section or light pipe (1) has a rigid structure.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
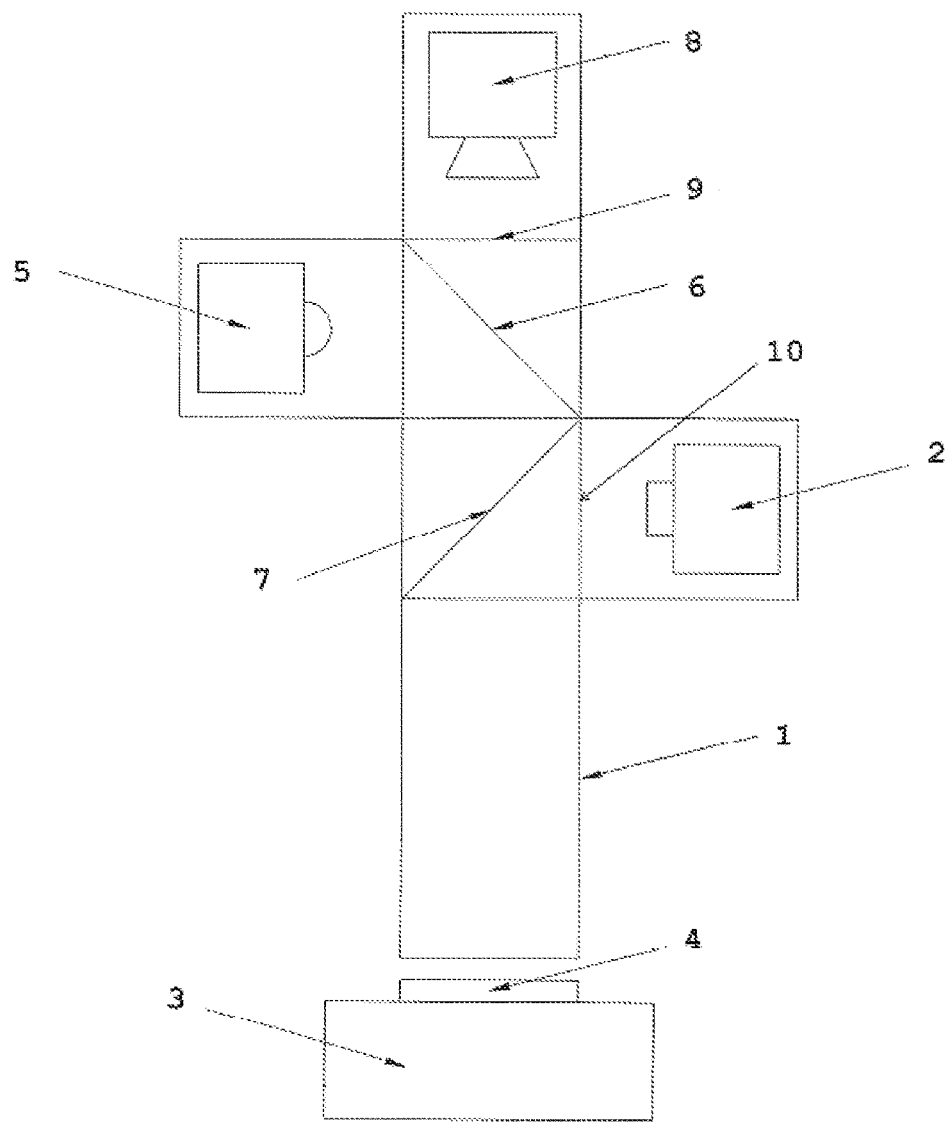
FIGS. 1-4 and 9-10 describe exemplary devices of the present invention.

The uniformity of electromagnetic radiation-based heating is critical for uniform, simultaneous and ultra-fast temperature cycling of samples at sample location (e.g. multiple samples), which is especially important for high-throughput applications (e.g. high-throughput PCR applications). Furthermore, accurate fluorescence detection of multiple reaction products in a thermal cycling device is only possible with homogenized (or uniform) illumination and uniform thermal cycling across samples. A source of electromagnetic radiation without uniformity-enhancing means facing a sample location comprising multiple samples in a thermal cycling device would unevenly deliver electromagnetic energy to different samples at the sample location and therefore unevenly heat said samples. Presence of additional optical devices within such a thermal cycling device would further complicate spatial constrains for delivering homogenized electromagnetic radiation at the sample location. The problem to be solved by the present invention is therefore inter alia to provide improved electromagnetic radiation-based thermal cycling devices free of the shortcoming known from conventional technology, especially when multiple sample are thermally cycled in an electromagnetic radiation-based thermal cycling device. The other problem to be solved by the present invention is to provide a thermal cycling device with improved power consumption and/or temperature control and/or wear and/or safety and/or costs characteristics.

In particular, the present invention addresses this problem in two ways: firstly, by providing efficient way of collecting and transmitting electromagnetic radiation and fluorescence excitation to a sample (e.g. multiple samples) at the sample location and secondly by providing means for effective cooling of parts that were heated by the remaining losses of radiated energy.

The problem is solved inter alia according to claims 1-15 and claims 16-25 of the present invention. Thus, the present invention advantageously provides means (e.g. light pipe section, light pipe) that are used to homogenize spatial intensity distribution of the heating electromagnetic radiation and therefore provide for a significant increase of uniformity of electromagnetic radiation-based heating. In one embodiment of the invention an achieved uniformity of electromagnetic radiation at the sample location is at least 90%. In another embodiment, an achieved uniformity of electromagnetic radiation at sample location is at least 95%. In another embodiment of the invention, an achieved uniformity of electromagnetic radiation at sample location is at least 98%. The present invention further provides devices, means and methods for uniform, simultaneous and ultra-fast temperature cycling of samples (or multiple samples, e.g. multiple PCR samples) that allow uniform, simultaneous and ultra-fast thermal cycling across said samples (e.g. up to 3.7 seconds PCR cycles, e.g. up to 7 seconds PCR cycles, e.g. in the range between 3 and 7 seconds PCR cycles). In another embodiment the present invention provides devices, means and methods for real-time fluorescence detection of reaction products, which enable monitoring reaction progress of samples. Advantageously, a thermal cycling device of the present invention comprises: a) a sample location (4); b) a first heating means (3), wherein said first heating means is configured to bring a sample at said sample location to at least about a first temperature; advantageously said first heating means is a contact heating means; c) a second heating means (2), wherein said second heating means is configured to bring said sample to a second temperature by directing electromagnetic radiation to the first light pipe section end and the light pipe section is configured to direct said electromagnetic radiation through its second end to the sample location (4). Thus, a presence of two heating means provides for rapid temperature change at the sample location, e.g. in that a baseline temperature (e.g. at least about a first temperature) is brought to a sample at sample location by a first heating means (3), whereas a second heating means (2) is configured to bring said sample to a second temperature (e.g. further heat up said sample from said baseline temperature). In one embodiment of the invention said second heating means is a source of electromagnetic radiation. In another embodiment "at least about a first temperature" is "first temperature" e.g. approximately annealing temperature of PCR primers. In one embodiment of the invention said first temperature does not equal said second temperature. In another embodiment of the invention said first temperature is less than said second temperature. In another embodiment of the invention said first temperature is below or equal to the temperature of the annealing of the PCR primers. In another embodiment of the invention said second temperature is a temperature of DNA denaturation (e.g. DNA denaturation of PCR amplification products). A light pipe (1) (or light pipe section) of the present invention is multifunctional because it allows to uniformly and simultaneously distribute electromagnetic energy from an electromagnetic heat source to samples and to uniformly and simultaneously illuminate said samples with light during said thermal cycling. In another embodiment of the invention light pipe provides means for uniformly, simultaneously and ultra-fast distributing the light for thermocycling, illumination and detection a multitude of independent reaction chambers. In another embodiment a light pipe (1) (or light pipe section) of the present invention is configured to homogenize spatial intensity distribution of electromagnetic radiation. In the course of the present invention the term "configured to" can have the meaning of directly or indirectly influencing the specified parameter (or parameters). In some embodiment of the invention said term "configured to" is selected to have the meaning of directly influencing the specified parameter (or parameters). In yet another embodiment of the invention the light pipe section has properties and/or dimensions of the light pipe (1) as described herein. In yet another embodiment the light pipe (or light pipe section) is an integral part of the thermal cycling device of the present invention.

In one embodiment of the invention light pipe (1) (or light pipe section) is a metal light pipe (or a metal light pipe section). In an embodiment of the invention light pipe (1) (or a light pipe section) is a hollow light pipe (or a hollow light pipe section). In a further embodiment of the invention light pipe (1) (or light pipe section) is metal hollow light pipe (or metal hollow light pipe section). In a most advantageous embodiment of the invention light pipe (1) (or light pipe section) is hollow and reflective. In another embodiment of the invention light pipe (1) (or light pipe section) has advantageously rectangular cross-section and is made from front surface mirrors. Alternatively, it is made from silver or gold coated solid metal to increase reflectivity. The hollow light pipe (1) (or light pipe section) of the present invention can be made from any material that can be coated by metal so that the surface is reflective and is able to withstand high power radiation. Alternatively, the material of the hollow light pipe (1) (or light pipe section) of the present invention has optical coating, so that it forms reflective dielectric mirror. In another embodiment of the invention light pipe (1) (or light pipe section) is a solid glass light pipe, however said solid glass light pipe might be associated with a light loss when entering the rod. In another embodiment of the invention the source of electromagnetic radiation (2) emits wavelength that is close to the wavelength of visible light, so that the surface of the light pipe (1) (or light pipe section) has similar properties for providing uniformity of heating with electromagnetic energy and uniformity of illumination. As the non-uniform electromagnetic energy and/or light emitted by a respective source enters the light pipe (1) (or light pipe section) it reflects many times from its surfaces and after each reflection the uniformity of the radiation and/or light is increased. However, in a common objective reflective walls are a major drawback because they reflect stray rays and distort the image, therefore objective producers usually make the walls of an objective black (i.e. not reflective). In yet another embodiment of the invention, the light pipe (or the light pipe section) of the present invention is not an objective (e.g. not an objective lens, e.g. not a 10x objective lens). In yet another embodiment of the invention, the light pipe (or the light pipe section) of the present invention is not circular. In one embodiment of the invention the uniformity of at least 90% (advantageously at least 95%, more advantageously greater than 95%) is achieved with the particular choice of the pipe length. In said embodiment of the invention the light pipe has the following dimensions: 16×17×150 mm and the achieved uniformity of electromagnetic radiation and light distribution at sample location is 90%. Two diode bars with diverging lens are used as sources of electromagnetic radiation and light. In further embodiment of the invention vertical diode stacks are used as sources of electromagnetic radiation and light. In one embodiment of the present invention the terms "light" (or "visible light") and "electromagnetic radiation" are selected not to overlap: the term "light" (or "visible light") is selected from the range of wavelengths that can be used to excite fluorescent dyes; thus the term "light" (or "excitation light") is selected from wavelengths that range from 100 nm to about 800 nm (e.g. less than 800, e.g. 799 nm); the excitation range overlaps with the emission (detection) range; the term "electromagnetic radiation" is selected from the range of wavelengths that can be used to heat up sample at sample location, advantageously used to heat water via absorption of the radiation, e.g. water starts absorbing at 500 nm, but advantageously practically useful lower limit is at approximately 800 nm (e.g. equals 800 nm or more than 800 nm). The upper limit for the heating range is practically unlimited, e.g. even 100 micrometers can be used. Therefore, in an embodiment the "light" is selected from excitation wavelengths in the range from 100 nm to about 800 nm (e.g. less than 800 e.g. 799 nm), whereas the "electromagnetic radiation" is selected from heating wavelengths in the range from 800 nm (e.g. equals 800 nm or more than 800 nm) to at least 100 micrometers. In one embodiment of the invention wavelength of 976 nm or 1470 nm is used for heating sample at sample location. Advantageously, absorption of radiation by water is very high at 1470 nm. In one embodiment of the invention 1470 nm wavelength is advantageously used for heating up samples at sample location (e.g. small aliquots of the PCR amplification mixture), and/or advantageously used for aliquots localized in a microfluidic device). On the other hand the absorption of light at 976 nm by water is much weaker. However, in another embodiment of the invention 976 nm wavelength is advantageously used to heat up larger sample volumes (e.g. containers of the PCR amplification mixture), and/or in applications in which the exact volume of the aliquots is not known. The disadvantage of using a wavelength that is more weakly absorbed is that most of the power emitted by the emitter is lost. The advantage, however, is that the sample is heated (absorbs) more uniformly along its height. In another embodiment of the invention the length of the light pipe approximately equals the pipe's side size, wherein said length of the pipe is defined as the optical length along which the light can be reflected off the walls of the pipe. In another embodiment of the invention a width of the pipe is the characteristic dimension of the cross-section of the pipe, perpendicular to the optical path. For square cross-sections, the width is the width of the square, for rectangular cross-sections there are two widths of the cross-section. In another embodiment of the invention light pipe (1) has a variable length (e.g. at least 2 cm, advantageously the length between 2 and 20 cm). In one embodiment of the invention light pipe (1) has a variable size and/or variable width. In an embodiment of the invention light pipe (1) has a width to length ratio of approximately 1, advantageously said width to length ratio is bigger than 3, more advantageously said width to length ratio is bigger than 5. In a further embodiment of the invention longer pipe is used if said pipe has good reflectivity because a longer pipe provides better uniformity. Circular pipes behave differently—they focus radiation and produce hot spot in the middle. Therefore, in yet another embodiment of the present invention the light pipe of the present invention, e.g. in a thermal cycling device of the present invention, cannot be a single circular pipe (e.g. wherein light pipe is not a circular pipe or wherein light pipe is not a single circular pipe). In another embodiment of the invention light pipe (1) comprises a chamber that has a reflective surface on one side and a semi-reflective surface on the other side in order to imitate a much longer section of pipe. This allows shortening of the light pipe (1), which is especially advantageous for large sample location (e.g. containers or holders) that would necessitate long pipes. In another embodiment of the invention light pipe (1) has inner surfaces that are reflective and that the volume enclosed by the pipe is transmissive (e.g. filled with gas, or with a different transparent material). In another embodiment of the invention the cross-section of the light pipe (1) is variable (e.g. square, hexagonal and rectangular). Sizes of the sample location (e.g. container) can be variable, e.g. 20×20 mm, 45×45 mm, and similar. Larger sizes are also possible are also encompassed by the present invention. In another embodiment of the invention sample location (4) (e.g. sample holder or sample container) is configured to receive multiple samples (e.g. 5, 7, 8, 10, 15, 20, 25, 30, 35, 40, 42, 45, 50, 55, 60, 65, 70, 75, 80, 85, 90, 95, 96, 100, 105, 110, 115, 120, 125, 130, 140, 145, 150, 155, 160, 165, 170, 175, 180, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 384, 385, 390, 395, 400 and so forth samples). The device of the present invention is not limited by the number of samples accommodated by sample location (4). In further embodiments the size of the sample location (4) is 20×20 mm or 45×45 mm, or similar dimension. In another embodiment of the invention sample location (4) (e.g. sample container or sample holder) is configured to receive a PCR microplate (e.g. 384-wells or 96-wells PCR plate) or 8-tubes strip or micro-fluidic chip containing 56 compartments of 0.6 µl and 8 compartments of 3.5 µl known from conventional technology. In another embodiment of the invention sample location (4) (e.g. sample container or sample holder) is configured to receive multiple samples (e.g. multiple PCR samples) and is placed on a first heating means (3) (e.g. heating block) or said sample location (4) is in contact with a first heating means (3) (e.g. thermal chamber) by the means of using e.g. heating/cooling with a gaseous or liquid medium. In another embodiment of the invention a first heating means (3) in addition to means of heating the samples further comprises means of cooling the samples (or sample) and/or means of stabilization of temperature. In another embodiment of the invention the device of the present invention comprises means of stabilizing the temperature at the sample location (4) (e.g. sample container or sample holder). In another embodiment of the invention camera (8) (e.g. used in detection) comprises an objective that only allows the light coming directly from the sample container (4) (or sample holder) to pass through (i.e. without any light reflected off the walls of the pipe). In another embodiment of the invention the positioning of the camera (8) and/or light source (5) (advantageously, excitation source) and/or electromagnetic heat source, wherein said electromagnetic heat source is a source of electromagnetic radiation (2) (advantageously, infrared (or IR) source) is variable (e.g. FIG. 1 and FIG. 2). In yet another embodiment of the invention the light pipe (or the light pipe section) of the present invention comprises inside at least one optical filter described herein (e.g. FIGS. 1-4, 9-10). This advantageously increases the efficiency and/or accuracy of the device of the present invention. As mentioned above, the light pipe (1) (or light pipe section) of the present invention is multifunctional because it allows to uniformly and simultaneously distribute electromagnetic energy from an electromagnetic heat source to multiple samples and to uniformly and simultaneously illuminate said multiple samples with light during said thermal cycling. Therefore, in yet another embodiment the light pipe (1) (or light pipe section) of the present invention comprises at least two reflective branches (e.g. for IR source, camera etc.) that are interconnected optically by an optical filter inside the light pipe (or light pipe section). Accordingly, in yet another embodiment the thermal cycling device of the present invention comprises such a light pipe (or the light pipe section), i.e. with at least one optical filter inside (e.g. FIGS. 1-4, 9-10). In another embodiment of the invention radiation source is placed directly above the entrance of the pipe (e.g. FIG. 2). In another embodiment of the invention the device of the present invention comprises at least one dichroic mirror (6), advantageously a set of dichroic mirrors (6, 7), more advantageously the dichroic mirror (6) is a multiband fluorescence dichroic mirror, and further advantageously dichroic mirrors (6 and 7) are multiband fluorescence dichroic mirrors. In another embodiment of the invention additional filter (9), e.g. fluorescence emission filter or e.g. multiband fluorescence emission filter, is positioned between the light pipe (1) and camera (8) (e.g. FIG. 1), advantageously said filter reflects IR and lets visible light pass. In another embodiment of the present invention an additional filter, e.g. fluorescence excitation filter or multiband fluorescence excitation filter, is positioned between the light pipe (1) and light source (5) (e.g. fluorescence excitation source), advantageously said excitation filter reflects infrared (IR) and let visible light pass.

In another embodiment of the invention dichroic mirror (7) reflects IR and lets visible light pass (e.g. FIG. 1). In another embodiment of the invention dichroic mirror (7) lets IR pass and lets visible light pass or reflects visible light selectively (e.g. FIG. 2). In another embodiment of the invention additional filter (10) reflects visible light and lets IR pass (e.g. FIG. 1). In another embodiment of the present invention dichroic mirror (7) lets IR pass and reflects visible light or selectively lets visible light pass (e.g. FIG. 2). In another embodiment of the present invention dichroic mirror (7) is a multiband fluorescence dichroic mirror (e.g. FIGS. 1 and 2). In another embodiment of the present invention dichroic mirrors (6 and 7) are multiband fluorescence dichroic mirrors (e.g. FIGS. 1 and 2). In another embodiment of the invention dichroic mirror (6) reflects visible light and lets IR pass (e.g. FIG. 2). In another embodiment of the invention (e.g. FIG. 1, or 3) a thermal cycling device comprises: a) a sample location (4); b) a first heating means (3), wherein said first heating means is configured to bring a sample at said sample location to at least about a first temperature; advantageously said first heating means is a contact heating means; c) a second heating means (2), wherein said second heating means is configured to bring said sample to a second temperature by directing electromagnetic radiation to the first light pipe section end (or advantageously to the first light pipe (1) end) and the light pipe section (or advantageously light pipe (1)) is configured to direct said electromagnetic radiation through its second end to the sample location (4); d) light source (5), advantageously said light source is a source of fluorescence excitation, e) at least one dichroic mirror (6), advantageously a set of dichroic mirrors (6, 7), more advantageously the dichroic mirror (6) is a multiband fluorescence dichroic mirror, more advantageously dichroic mirrors (6 and 7) are a multiband fluorescence dichroic mirrors; further advantageously dichroic mirror (7) reflects IR and lets visible light pass; f) camera (8), advantageously said camera is an emitted fluorescence light detection camera; g) at least one fluorescence filter (9), advantageously said fluorescence filter is an emission filter, more advantageously said at least one fluorescence filter is multiple fluorescence filters, most advantageously said at least one fluorescence filter is a multiband fluorescence filter, further advantageously said at least one fluorescence emission filter is a multiband fluorescence emission filter; further advantageously filter (9) is positioned between camera (8) and the light pipe (1) (e.g. FIG. 1); h) optionally an additional filter (10), advantageously wherein said additional filter reflects wavelengths below infrared; further advantageously said additional filter (10) reflects visible light and lets IR pass; further advantageously filter (10) is positioned between second heating means (2) and light pipe (1) (e.g. FIG. 1); i) optionally an additional excitation filter (11), advantageously positioned between light source (5) and the light pipe (1) (e.g. FIG. 3); further advantageously said excitation filter is a multiband fluorescence excitation filter.

In another embodiment of the invention (e.g. shown in FIG. 2 or 4) a thermal cycling device comprises: a) a sample location (4); b) a first heating means (3), wherein said first heating means is configured to bring a sample at said sample location to at least about a first temperature; advantageously said first heating means is a contact heating means; c) a second heating means (2), wherein said second heating means is configured to bring said sample to a second temperature by directing electromagnetic radiation to the first light pipe section end (or first light pipe (1) end) and the light pipe section (or light pipe (1)) is configured to direct said electromagnetic radiation through its second end to the sample location (4); d) light source (5), advantageously said light source is a source of fluorescence excitation; e) at least one dichroic mirror (6), advantageously, said at least one dichroic mirror (6) reflects visible light and lets IR pass; further advantageously a set of dichroic mirrors (6, 7), more advantageously the dichroic mirror (6) is a multi-band fluorescence dichroic mirror, further advantageously the dichroic mirrors (6, 7) are multiband fluorescence dichroic mirrors; further advantageously mirror (7) lets IR pass and lets visible light pass or reflects visible light selectively; f) camera (8), advantageously said camera is an emitted fluorescence light detection camera; g) at least one fluorescence filter (9), advantageously said fluorescence filter is an emission filter, more advantageously said fluorescence filter is multiple fluorescence filters, most advantageously said at least one fluorescence filter is a multiband fluorescence filter, further advantageously said at least one fluorescence emission filter is a multiband fluorescence emission filter; further advantageously said filter (9) is positioned between camera (8) and the light pipe (1); further advantageously filter (9) reflects IR and lets visible light pass; h) optionally an additional excitation filter (11), advantageously positioned between light source (5) and the light pipe (1) (e.g. FIG. 4); further advantageously said excitation filter is a multiband fluorescence excitation filter; further advantageously said excitation filter reflects IR and lets visible light pass. In another embodiment of the present invention fluorescence detection by camera does not use reflections from inner wall of the light pipe (advantageously camera does not detect said reflections and is configured in such a way as to detect only fluorescence coming directly from the sample, without being reflected off the walls of the pipe, for example by using telephoto lens or diaphragm). In another embodiment of the invention the device of the present invention comprises at least one fluorescence filter (9), advantageously said fluorescence filter is an emission filter, more advantageously multiple fluorescence filters, most advantageously said at least one fluorescence filter is a multiband fluorescence filter. In another embodiment of the invention the device of the present invention comprises excitation filter which is positioned right after light source (5) (e.g. right after excitation source e.g. between excitation source and the light pipe). In another embodiment of the invention the device of the present invention comprises a filter for radiation source, advantageously positioned e.g. right between a source of electromagnetic radiation and the light pipe. In another embodiment of the invention an excitation and/or emission fluorescence filters and/or dichroic mirrors are optionally multiband. In another embodiment of the invention an excitation filter and/or emission fluorescence filter and/or dichroic mirrors of the present invention let IR pass. In another embodiment of the invention a device of the present invention doesn't comprise fluorescence detection, in which case dichroic mirror (7) is redundant and is not present in the device of the present invention. In yet another embodiment of the invention additional optical filters that are designed to retain light pipe's function by reflecting desired wavelength are used at locations where there might be a hole in the wall of the light pipe—e.g. in FIG. 1 it might be filter (10), while e.g. in FIG. 2 excitation filter (e.g. between camera and light pipe) and/or emission filter (e.g. between light source and light pipe) can have this functionality. In another embodiment of the invention the device of the present invention comprises many light pipes, each containing a separate source of electromagnetic radiation, connected to the main, larger light pipe that ultimately heats the sample (or samples). In another embodiment of the invention no detection is carried out and radiation source is placed above (e.g. directly above) the entrance (e.g. first end) of the light pipe. In another embodiment of the invention the device of the present invention provides means of detection of the reaction progress during thermal cycling (advantageously means of real time detection, further advantageously means of real-time fluorescence detection of PCR amplification). In another embodiment of the invention the device of the present invention comprises a laser source as a source of electromagnetic radiation (2). In another embodiment of the invention a one axis—diverging lens (e.g. in the shape of half a cylinder) is used right on the IR source (e.g. IR diode). The IR diode emits differently in the two directions in the plane of the diode. The light is collimated in one direction, while it is strongly divergent in the other direction. The beam coming from IR source is therefore diverged in the direction in which it was originally collimated in order to obtain as uniformly divergent beam as possible. Therefore, the beams are configured to have a similar number of reflections in all the directions before they hit the sample (or samples). In another embodiment of the invention the device of the present invention comprises transparent glass window at one end of the pipe in order to protect the device from dust. In another embodiment of the invention an additional filter is added to the device of the present invention to reflect the excitation light from the aperture that allows the IR illumination in (or vice-versa if the IR-source is placed above the excitation source).

In another embodiment the device of the present invention comprises a high power (e.g. hundreds of Watts) halogen lamp (e.g. multiple halogen lamps) instead of a laser source as a second heating means (2) (e.g. as a source of electromagnetic radiation (2)). This advantageously allows to achieve fast thermal cycling over a large area and reduces the costs since a laser source is over 100 times more expensive than a halogen lamp per Watt of power. The area is considered large from a microfluidic point of view if it covers multiple microfluidic compartments (e.g. the large area can be 23×26 mm2, advantageously, side length may be between 1 and 200 mm). Necessitated amount of power of such a high power halogen lamp depends on a necessitated rate of heating, pipe exit surface area and microfluidic compartment depth that influences absorption efficiency and can be easily calculated by a person skilled in the art using standard methodology. The rate of heating of such a high power halogen lamp can be between 1 and 1000 K/s and advantageously between 3 and 100 K/s. In an embodiment two Osram HPL 93729 LL 750 W 230 V halogen lamps are used, each having 750 W to reach 20 K/s heating rate in microfluidic compartments that are 400 µm deep.

Figure 9:
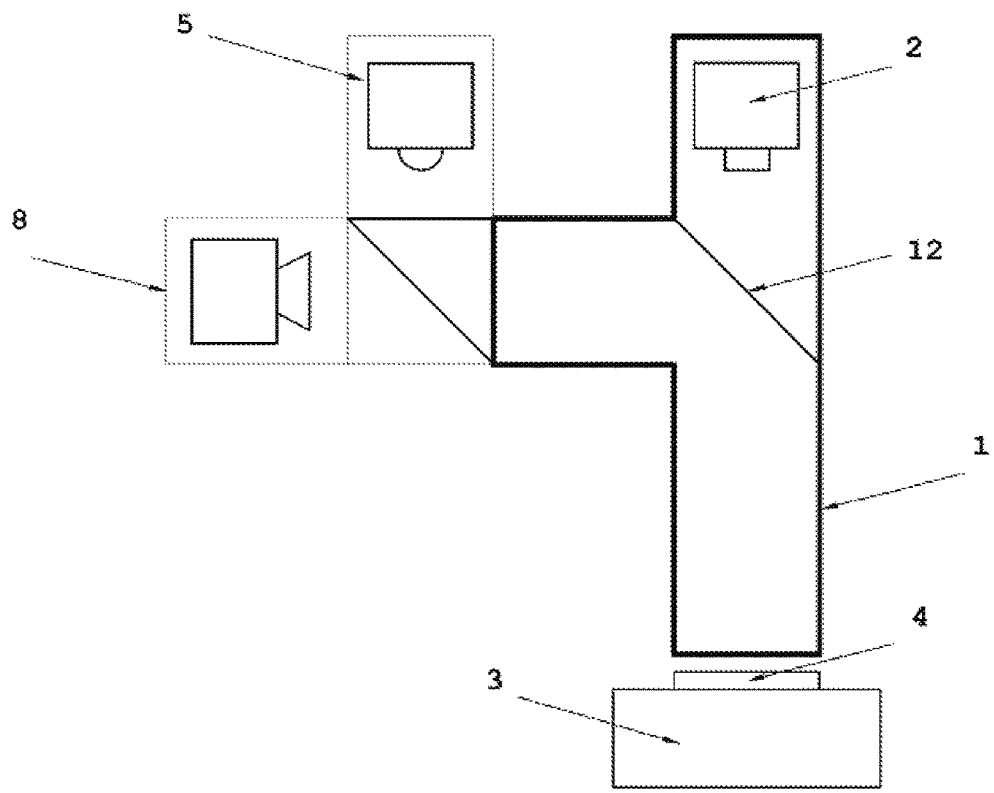
Figure 10:
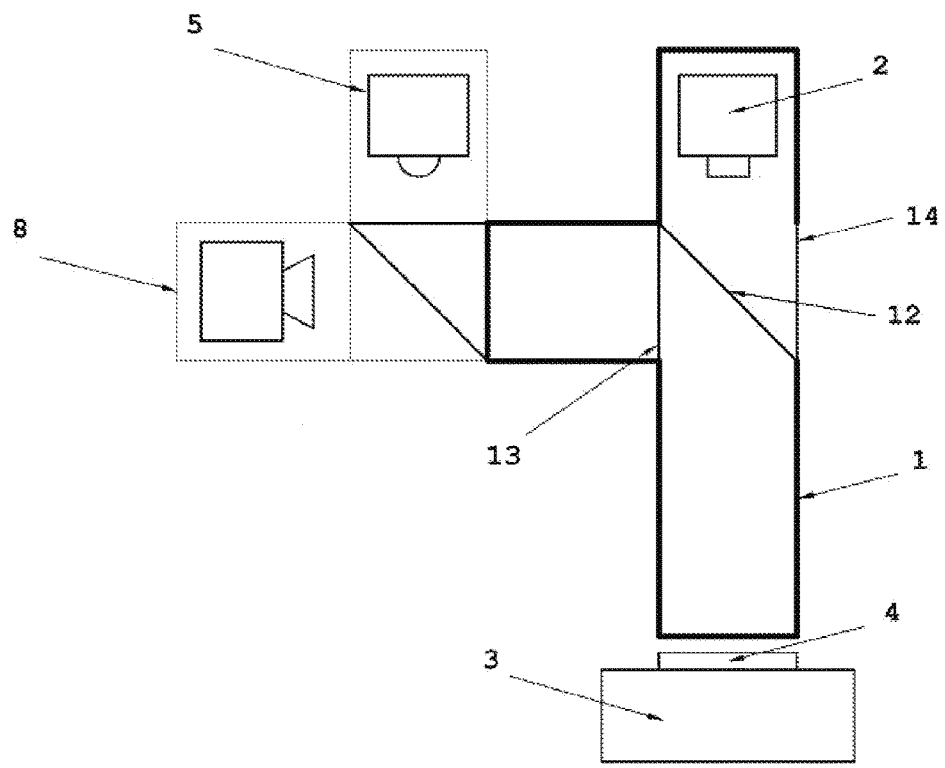

In another embodiment the device of the present invention comprises a halogen lamp (or lamps) of the present invention that is an omnidirectional source of energy that is enclosed within the light pipe of the present invention (advantageously with one end of the light pipe closed, e.g. the end where the halogen lamp is located) to significantly increase efficiency of the device of the present invention (e.g. FIGS. 9 and 10).

In another embodiment the device of the present invention comprises means of completely blocking electromagnetic radiation, e.g. a mechanical shutter that completely blocks electromagnetic radiation when closed. The mechanical shutter of the present invention, for example, can be a metal plate that slides (e.g. horizontally) into an opening (e.g. slit) in the wall of the light pipe (or the light pipe section) of the present invention, e.g. by the means of a computer-controlled electric motor. Advantageously the plate can be polished to reduce thermal heating. The use of a mechanical shutter in the device of the present invention is especially beneficial in order to achieve accurate thermal cycling (e.g. accurate control over parameters that influence PCR cycle such as halogen on time) with a halogen lamp (or lamps) as a source of electromagnetic radiation (2) since a halogen lamp can have large thermal inertia and long switching times (e.g. high power halogens need hundreds of milliseconds to stabilize their filament temperature and consequently radiated power when turned on or off). However, the use of a mechanical shutter in the device of the present invention is also beneficial when laser diodes are used as a source of electromagnetic radiation (2) because frequent switching of laser diodes causes thermal strain in the diode structure and therefore quickens its aging.

In another embodiment the device of the present invention comprises means of cooling of the light pipe or a light pipe section (e.g. first, second or third) of the present invention (advantageously external means of cooling). Thus, due to increased power the losses of electromagnetic radiation can cause substantial heating of the light pipe (or a light pipe section) over time, e.g. if the light pipe (or a light pipe section) is not provided with external means of cooling it can heat up over 200 degrees Celsius if halogen is constantly turned on. However, this problem can be advantageously solved by the means of cooling (e.g. air or liquid cooling) of the light pipe (or the light pipe section) in case of the high thermal conductivity of the light pipe material, which inter alia increases safety profile of the device of the present invention.

Halogens have wide spectrum of radiation that extends approximately from 300 nm to 4000 nm and for this reason it can be difficult to obtain optical filters (e.g. filters to be placed inside the light pipe (or light pipe section) as described herein) that would have necessitated characteristics.

Therefore, in another embodiment the device of the present invention comprises a longpass optical filter (12) (e.g. FIG. 9). Such a longpass optical filter (12) can, for example, divide a detection and heating parts of the device of the present invention (e.g. FIGS. 9, 10). The longpass optical filter (12) of the present invention, for example, reflects visible light and lets infrared light pass. Advantageously, a longpass optical filter (12) of the present invention is a dichroic mirror, e.g. 650 nm, 25.2×35.6 mm, dichroic longpass filter No. 69-902 from Edmund Optics.

In another embodiment the device of the present invention comprises a longpass optical filter (12), an optional filter (13) that can, for example, compensate for an opening (e.g. a hole) in the wall of the light pipe (or the light pipe section) of the present invention by reflecting IR radiation and letting visible light pass and an optional filter (14), which e.g. can be of exactly the same type as filter (13) and that can, for example, be used to increase symmetry of the light pipe caused by non-ideal behavior of filter (13) and serves to increase uniformity of radiation (e.g. FIG. 10). This embodiment is particularly advantageous in that it allows the use of an off-the-shelf fluorescence filter cube, which has multiband filters. In one embodiment longpass optical filter (12) can, for example, reflect electromagnetic radiation and let visible light pass to improve device efficiency.

In a particular embodiment, a device of the present invention comprises: a first heating means (3), a sample location (4), a light pipe (1), a second heating means (2), a light source (5), a camera (8) and a longpass optical filter (12) (e.g. FIG. 9). In another particular embodiment, a device of the present invention comprises: a first heating means (3), a sample location (4), a light pipe (1), a second heating means (2), a light source (5), a camera (8), a longpass optical filter (12), an optional filter (13) and an optional filter (14) (e.g. FIG. 10).

As mentioned above, the conventional technology teaches to expedite cooling of sample enclosed in a microfluidic chip by the means of Peltier element. However, control over temperature of the thermal block is not sufficient to accurately change sample temperature during thermal cycling. A parameter that is equally important is thermal contact conductance that influences significantly rate of heat transfer, especially during fast thermal cycling. The thermal contact conductance coefficient has ordinary meaning known in the art and describes ability to conduct heat between two bodies in contact. The factor of most influence on the value of thermal contact conductance parameter is the contact pressure. For example, contact pressure results from force acting on surface of microfluidic chip when it is pressed to the heating block. The pressure can be around 0.1-100 MPa. The present invention, in particular, provides a way to control value of thermal contact conductance by the means of pressure exerted through the rigid structure of the light pipe assembly (or light pipe section assembly) in a manner that allows for shortest possible distance between the chip and the light pipe (or a light pipe section) and facilitates loading of the chip to the device of the present invention. Thus, during the course of the present invention it was surprisingly observed that increase in the pressure exerted on the sample location (4) (e.g. microfluidic chip) in the device of the present invention causes faster cooling of the sample location (4) (e.g. multiples samples). Moreover, if the sample location (4) (e.g. a chip, a microfluidic chip) is put on the first heating means (3) (e.g. a heating block) with no pressure applied, differences in heating rate between different chips, which e.g. result from non-ideal repeatability of chip production process, might occur. This problem can be advantageously solved using interstitial material that fills microscopic gaps between a sample location (e.g. chip) and first heating means (3) (e.g. heating block) such as mineral oil or by the means of external pressure applied on the sample location (or both), which are embodiments of the present invention. Therefore, in one embodiment the device of the present invention comprises a light pipe (or a light pipe section) of rigid structure and means for moving the light pipe (or the light pipe section) (e.g. vertically) and exerting force (e.g. constant force) on the sample location (4). Any means that can move the light pipe (or a light pipe section) and exert force in the range from 1 to 10000 N on the sample location (4) is suitable (e.g. a mechanical drive). Necessitated force depends on desired contact pressure. Example means for moving the light pipe (or a light pipe section) (e.g. mechanical drives) that can be used in the device of the present invention is a linear screw actuator or a linear motor. The light pipe (or a light pipe section) of rigid structure can, for example, be made from a thick metal (approximately 3 mm), and can directly press (e.g. constantly press) the sample location (4) (e.g. a microfluidic chip) without bending or breaking with a force in the range from 1 to 10000 N. A person skilled in the art can easily assess if the light pipe assembly (or light pipe section) can be safely operated with such force. In an embodiment the device of the present invention comprises a mechanical drive and a light pipe (or a light pipe section) of rigid structure to directly press a microfluidic chip to the first heating means (3) (e.g. a thermal block) with a controlled force (e.g. constant force) in the range from 1 to 10000 N. This approach has multiple advantages, e.g. firstly, it compensates for inaccuracies of the chip surface, secondly, it allows for rapid heat transfer during cooling and/or heating and thirdly, it allows for easy chip placement under the light pipe (or the light pipe section) of the present invention. In another embodiment a device of the present invention comprises a plate positioned between the light pipe (or the light pipe section) of the present invention and the sample location (4). Thus, to press more evenly such a plate (e.g. a glass plate, a thick glass plate) at the end of the light pipe (e.g. at the end that is in contact with (or closest to) the sample location (4)) can be used in the device of the present invention that also protects the device of the present invention from dust. In the absence of such a plate the light pipe (or the light pipe section) of the present invention presses the sample location (4) (e.g. a microfluidic chip) with its sides only, which in case of a non-perfectly flat sample location (4) (e.g. a microfluidic chip), can cause lack of physical contact with a first heating means (3) (e.g. heating block) in the middle of the sample location (4) (e.g. microfluidic chip) and consequently differences in heat transfer across the sample location (4). The necessitated thickness of the plate is largely dependent on pressure. Exemplary thickness is between 0.5 and 10 mm and advantageously between 1 and 5 mm. The material of the plate that presses sample location (4) (e.g. a microfluidic chip) is rigid and at least partially translucent. Alternatively, a sample location (4) (e.g. a microfluidic chip) can be pressed with a metal plate that has openings over microfluidic compartments to allow electromagnetic radiation pass. Alternatively, a sample location (4) (e.g. microfluidic chip) can still be pressed using edges of the light pipe (or the light pipe section) of the present invention.

In one embodiment the present invention provides a thermal cycling device comprising: a) a sample location (4); b) a light pipe section comprising a first and a second end, wherein said light pipe section is configured to homogenize spatial intensity distribution of electromagnetic radiation by the means of reflection, advantageously the reflectance is bigger than 50%, further advantageously bigger than 90%; c) a first heating means (3), wherein said first heating means is configured to bring a sample at said sample location to at least about a first temperature; advantageously said first heating means is a contact heating means; d) a second heating means (2), wherein said second heating means is configured to simultaneously bring multiple samples at said sample location to a second temperature by directing electromagnetic radiation to the first light pipe section end and the light pipe section is configured to direct said electromagnetic radiation through its second end to the sample location (4); e) optionally, means of completely blocking electromagnetic radiation, advantageously a mechanical shutter that completely blocks electromagnetic radiation when closed; f) optionally, means of cooling of said light pipe section (or means of cooling of the light pipe), advantageously means of external cooling; g) optionally, a longpass optical filter (12); h) optionally, additional filter (13); i) optionally, additional filter (14); j) optionally, means for moving the light pipe section (or means for moving the light pipe) and exerting force on the sample location (4); k) optionally, a plate positioned between the light pipe section (or the light pipe) and the sample location (4).

In another embodiment the present invention provides a thermal cycling device comprising: a) a sample location (4); b) a first light pipe section at least operable to collect electromagnetic radiation, advantageously from at least one halogen lamp; c) a second light pipe section at least operable to collect fluorescent excitation and transmit fluorescence emission light, advantageously said second light pipe section is configured to homogenize the fluorescent excitation intensity; d) a third light pipe section at least operable to illuminate said sample location (4) with electromagnetic radiation and fluorescent excitation and to transmit fluorescent emission light to the second light pipe section, advantageously said third light pipe section is configured to homogenize the fluorescent excitation intensity; e) an optical filter configured to reflect visible light and transmit electromagnetic radiation; wherein at least one light pipe section is configured to homogenize spatial intensity distribution of light and electromagnetic radiation by the means of reflection, advantageously each light pipe section is configured to homogenize spatial intensity distribution of light and electromagnetic radiation by the means of reflection, further advantageously the reflectance is bigger than 50%, most advantageously the reflectance is bigger than 90%; f) optionally, means of completely blocking electromagnetic radiation, advantageously a mechanical shutter that completely blocks electromagnetic radiation when closed; g) optionally, means of cooling of at least one light pipe section (or means of cooling of the light pipe), advantageously means of external cooling; h) optionally, a longpass optical filter (12); i) optionally, additional filter (13); j) optionally, additional filter (14); k) optionally, means for moving the light pipe section (or means for moving the light pipe) and exerting force on the sample location (4); l) optionally, a plate positioned between the third light pipe section (or the light pipe) and the sample location (4). In another embodiment the present invention provides the thermal cycling device of the present invention further comprising a light pipe (1), wherein said light pipe (1) comprises said first, second and third light pipe sections.

In another embodiment the present invention a fluorescent excitation intensity is homogenized at least by a third light pipe section, wherein a second light pipe section is only advantageously configured to homogenize said intensity of fluorescent excitation.

In another embodiment the present invention provides the thermal cycling device of the present invention, further comprising: a first heating means (3), advantageously said first heating means is configured to bring a sample (or multiple samples) at said sample location to at least about a first temperature; a second heating means (2), wherein said second heating means (2) is a source of electromagnetic radiation, advantageously said second heating means is configured to bring said sample (or multiple samples) to a second temperature; a light source (5), advantageously said light source is a source of fluorescence excitation; and a camera (8), advantageously said camera is an emitted fluorescence light detection camera. In another embodiment the present invention provides the thermal cycling device of the present invention, wherein: a) said first light pipe section is at least operable to collect electromagnetic radiation from said second heating means (2); b) said second light pipe section is at least operable to collect fluorescent excitation from said light source (5) and transmit a fluorescence emission light from said third light pipe section to said camera (8); c) said third light pipe section is at least operable to illuminate said sample location (4) with said electromagnetic radiation and said fluorescent excitation and to transmit said fluorescent emission light from said sample location (4) to said second light pipe section. In another embodiment the present invention provides the thermal cycling device of the present invention, wherein said first heating means (3) is a contact heating means. In another embodiment the present invention provides the thermal cycling device of the present invention, wherein at least one of said first, second or third light pipe sections is made of metal, advantageously to facilitate cooling of said light pipe section, e.g. external cooling, and/or to provide structural rigidness that can be used to press sample location (4), e.g. microfluidic chip, to first heating means, e.g. thermal block.

In another embodiment the present invention provides the thermal cycling device of the present invention, wherein said light pipe (1) is made of metal, advantageously to facilitate cooling of said light pipe, e.g. external cooling, and/or to provide structural rigidness that can be used to press sample location (4), e.g. microfluidic chip, to first heating means, e.g. thermal block.

In another embodiment the present invention provides the thermal cycling device of the present invention, wherein said third light pipe section or said light pipe (1) is configured to press said sample location (4) to said contact heating means (3). In another embodiment the present invention provides the thermal cycling device of the present invention, wherein said light pipe (1) is configured to press said sample location (4) to said contact heating means (3). In another embodiment the present invention provides the thermal cycling device of the present invention, wherein at least said third light pipe section or light pipe (1) has a rigid structure.

In yet another embodiment of the present invention the light pipe (advantageously hollow light pipe) or the light pipe section (advantageously hollow light pipe section) (e.g. first, second or third) of the present invention is capable of transmitting (or directing) light (e.g. fluorescent excitation from the light source (5) and fluorescent emission from the sample location (4)) in both directions (e.g. to and from the sample location (4), which is particularly advantageous for fluorescence detection. It is a particular advantage of the use of a hollow light pipe of the present invention—although the light pipe homogenizes spatial intensity distribution of fluorescence excitation, it is possible to directly observe emitted fluorescence from the sample location (4) (e.g. microfluidic chip) (e.g. without reflections from the sides of the light pipe) if one looks straight through the light pipe.

In another embodiment of the invention thermal cycling is PCR thermal cycling (real-time PCR thermal cycling or digital PCR thermal cycling). In another embodiment of the invention a thermal cycling device is a PCR thermal cycling device (real-time PCR thermal cycling device or digital PCR thermal cycling device). In further embodiment of the invention a sample (or samples) is a PCR sample (or PCR samples) (e.g. PCR reaction mixtures) (real-time PCR samples or digital PCR samples). Real-time PCR is extremely sensitive to the non-uniform thermal cycling and therefore uniformity of thermal cycling is crucial for an accurate and reliable real-time PCR procedure (or method). In further embodiment of the invention a device of the present invention comprises a fluorescence detection unit. The uniformity (or homogeneity) of illumination is also crucial for the fluorescence detection (e.g. in real time PCR), because it allows to quantitatively compare fluorescence intensities between samples at different locations in the container. In another embodiment of the invention the use of the light pipe of the present invention (e.g. hollow metal pipe) enables to use optical elements, e.g. such as dichroic mirrors, within the light pipe, which creates a safety barrier between fluorescence detection unit and a source of electromagnetic radiation. In further embodiment of the invention dichroic mirror (7) is used to reflect electromagnetic radiation while letting the excitation and emission fluorescence light pass. In another embodiment of the invention dichroic mirror (6) is used to reflect excitation light and lets emission light pass. In another embodiment of the invention emission filter (9) is used to further block stray excitation light while letting emission light pass. In another embodiment of the invention the device of the present invention optionally comprises an additional filter (10), wherein said additional filter reflects wavelengths below infrared (FIG. 1). In another embodiment of the invention filter (10) is used to retain the function of the light pipe in spite of the hole in its wall. In another embodiment of the present invention the device of the present invention comprises dichroic mirror (6) and/or emission filter (9), which are multiband fluorescence filters to enable simultaneous detection of many dyes, for example DA/FI/TR/Cy5-A-000 filter set from Semrock, which enables detection of DAPI, FITC, TRITC and Cy5. In another embodiment of the present invention the device of the present invention comprises multiband dichroic mirrors for multiplexed detection of products of PCR amplification, eliminating the need for multiple single-band dichroic mirrors and precise mechano-optics for aligning the light from multiple LED sources. In another embodiment of the invention the light source (5) (e.g. fluorescence excitation light source) is RGB LED (red, green, and blue light-emitting diodes). In another embodiment of the invention the light source (5) (e.g. fluorescence excitation light source) is a multitude of light sources of different types, which does not compromise illumination quality because non-uniformity of the light source is completely reduced by the use of light pipe of the present invention, e.g. metal light pipe. In yet another embodiment of the invention the device of the present invention comprises multiband filters (9) that enable detection of a temperature-sensitive fluorescence dye, for example Rhodamine B, thus allowing to measure temperature of the sample in real-time during the PCR. In another embodiment the invention provides a method for controlling temperature of samples in real time during thermal cycling, said method comprising: keeping the source of fluorescence excitation (5) on or turning it on periodically while simultaneously reading fluorescence excitation changes caused by change of temperature using the camera (8) during the thermal cycling. The temperature readings of the samples allow to set heating and cooling times described in the methods of the present invention. In another embodiment the present invention provides a method for uniform simultaneous and ultra-fast amplification of samples (e.g. multiple samples) with PCR, said samples comprising nucleic acid or fragment thereof, combined with real-time detection of amplified products (e.g. PCR products) using intercalating dies such as e.g. SybrGreen. In another embodiment the present invention provides a method for uniform and simultaneous amplification of samples with PCR, said samples comprising a nucleic acid or a fragment thereof, combined with real-time detection of amplified product, said method comprising:

(a) maintaining the temperature of the first heating means (3) at a specific temperature (e.g. at 55° C. or e.g. 55° C.±10° C. or e.g. 55° C.±15° C.), wherein said specific temperature is below or equal to the temperature of the annealing of the PCR primers;

(b) while maintaining said temperature constant, turning on the source of electromagnetic radiation (2) at a constant power for a specified period of time (e.g. 15 W total power for 2 seconds), wherein uniformly and simultaneously heating said samples until they reach the temperature of DNA denaturation;

(c) while still maintaining the temperature of the first heating means (3), turning off the source of electromagnetic radiation (2) for a specified period of time (e.g. 5 seconds), wherein cooling said samples (rapidly cooling said samples, e.g. at a rate of 6° C./second or at a rate 15° C./second); repeating steps (b)-(c) at least 15 times, more advantageously repeating steps (b)-(c) at least 20 times, most advantageously repeating steps (b)-(c) at least 30 times; further advantageously repeating steps (b)-(c) at least 40 times; further advantageously repeating steps (b)-(c) at least 60 times;

(d) after specified period of time (e.g. 4 seconds from the end of stage b)) turning on the source of fluorescence excitation, wherein uniformly and simultaneously exciting said samples, and simultaneously performing detection of emitted fluorescence light using the camera (8).

In another embodiment of the present invention a constant thermal gradient is created in the first heating means (3) (e.g. heating block) during PCR, (for example left side is set to be at 50° C. and right side—at 60° C. with intermediary temperatures in-between). During PCR cycling a source of electromagnetic radiation provides the same amount of power to each sample, but the temperature of the first heating means (3) (e.g. heating block) is different for each one of them, thus they experience different cycling conditions (e.g. different annealing temperatures). After PCR is performed a user may check which cycling conditions had been optimal (e.g. verified by large amount of a specific product) and then use optimum temperature (e.g. optimum annealing temperature) of the first heating means (3) (e.g. heating block) for future experiments. In another embodiment of the present invention different PCR temperatures (i.e. different annealing temperatures in a method of the present invention) are run in parallel in the first heating means (3). In another embodiment of the invention temperature of the first heating means (3) is used to eliminate (or compensate for) any non-uniformities in sample temperature at the sample location caused by residual non-uniformities in radiation distribution intensity at sample location by introducing spatial changes in temperature of the first heating means (3) (e.g. heating element). In another embodiment of the invention methods steps (b)-(c) comprise one PCR cycle and are repeated periodically until the cycle count reaches specified (e.g. desired) number. In another embodiment of the invention the sample location (4) (e.g. sample container or sample holder) is a microfluidic chip containing multitude of compartments. In further embodiment, it is a PCR microplate, which is e.g. pippeted by skilled operator or a robot. The invention is further supported by the following Examples and Figures without being limited to said Figures and Examples.

Modes for Carrying Out the Invention Including a Best Mode of Carrying the Invention

EXAMPLES OF THE INVENTION

FIGS. 1-4 and 9-11 provide exemplary non-limiting embodiments of the present invention:

FIG. 1 describes an exemplary device of the present invention comprising: a first heating means (3), wherein the first heating means (3) is a heating block, a sample location (4), a light pipe (1), a second heating means (2), wherein the second heating means (2) is a source of radiation, a light source (5), a camera (8), a dichroic mirror (6), a dichroic mirror (7), wherein at least the dichroic mirrors (6, 7) are placed inside the light pipe (1), a fluorescence filter (9) and an additional filter (10), wherein said additional filter (10) reflects wavelengths below infrared.

Figure 2:
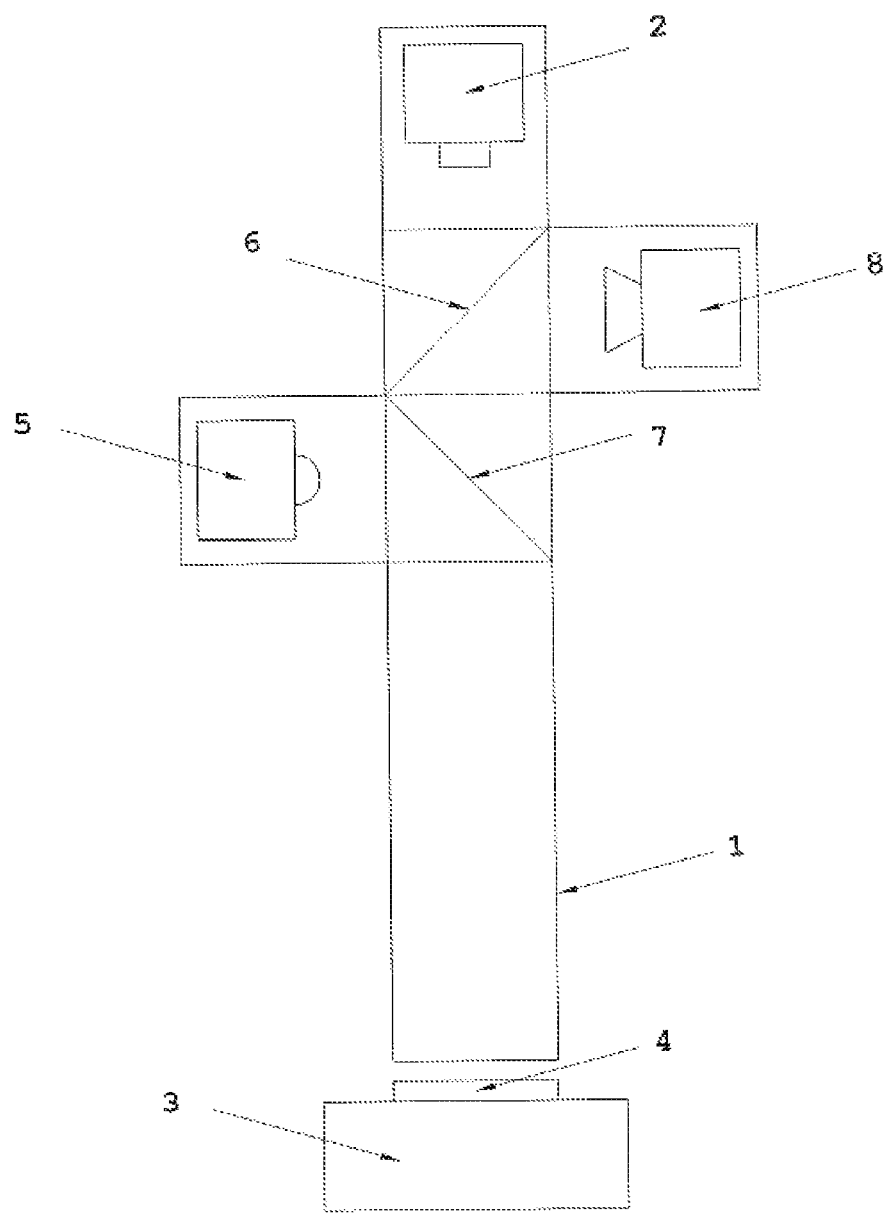

FIG. 2 describes an exemplary device of the present invention comprising: a first heating means (3), wherein the first heating means (3) is a heating block, a sample location (4), a light pipe (1), a second heating means (2), wherein the second heating means (2) is a source of radiation, a light source (5), a camera (8), a dichroic mirror (6) and a dichroic mirror (7), wherein at least the dichroic mirrors (6, 7) are placed inside the light pipe (1).

Figure 3:
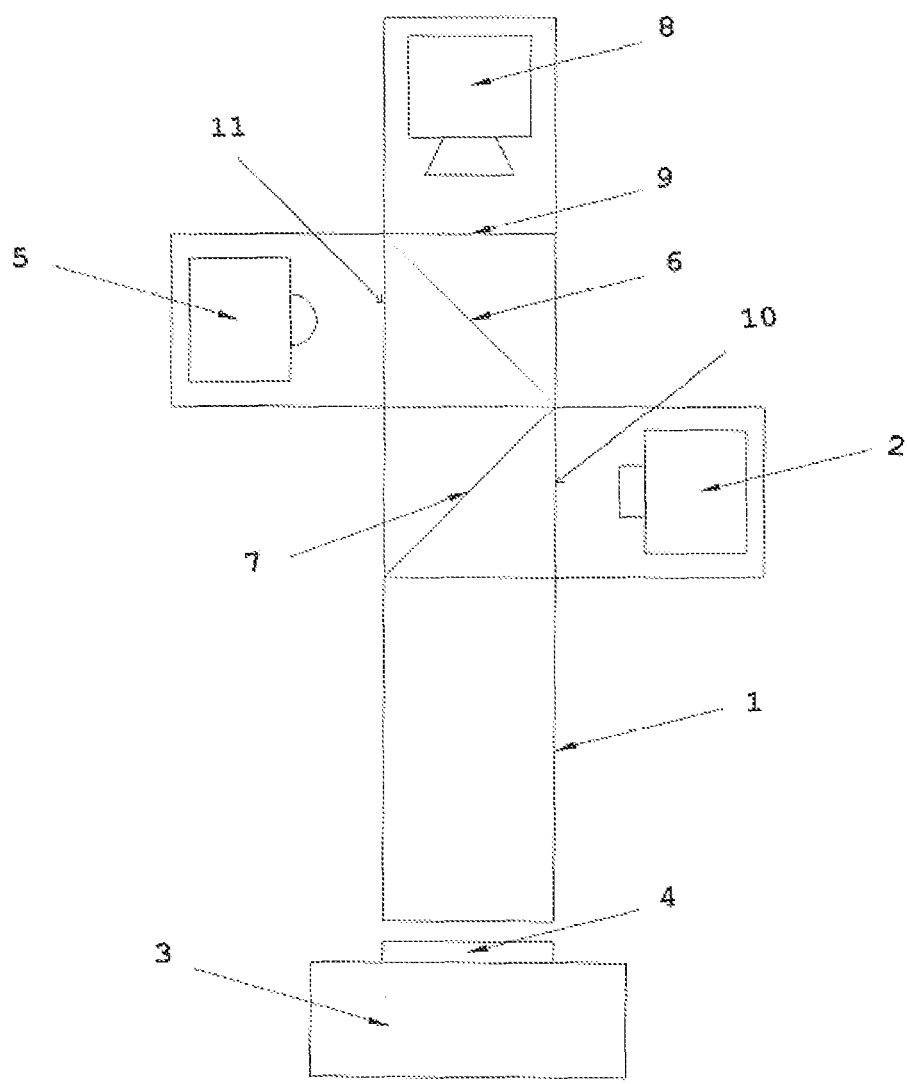

FIG. 3 describes a best mode of carrying the invention—an exemplary device of the present invention comprising: a first heating means (3), wherein the first heating means (3) is a heating block, a sample location (4), a light pipe (1), a second heating means (2), wherein the second heating means (2) is a source of radiation, a light source (5), a camera (8), a dichroic mirror (6), a dichroic mirror (7), wherein the dichroic mirrors (6, 7) are placed inside the light pipe (1), a fluorescence filter (9), an additional filter (10), wherein said additional filter (10) reflects wavelengths below infrared, and an excitation filter (11).

Figure 4:
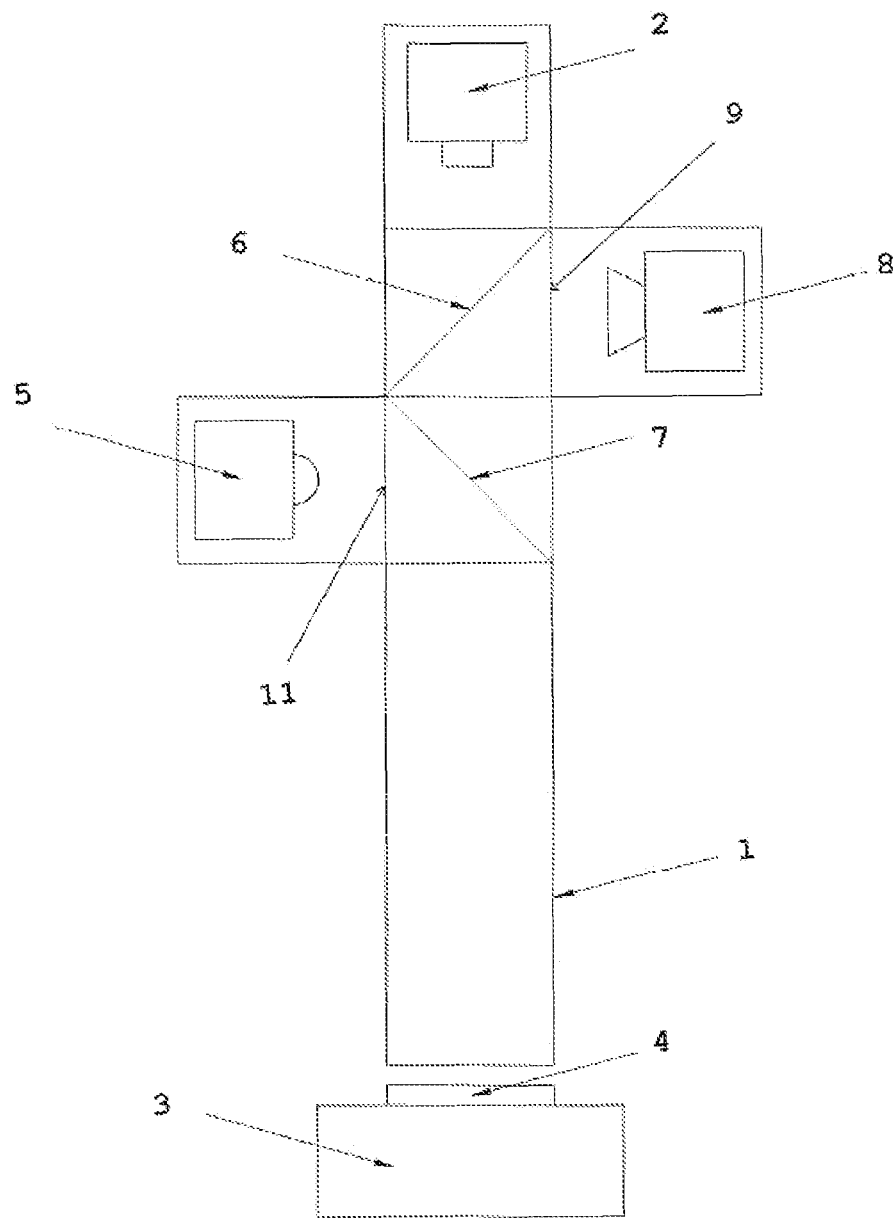
Figure 5:
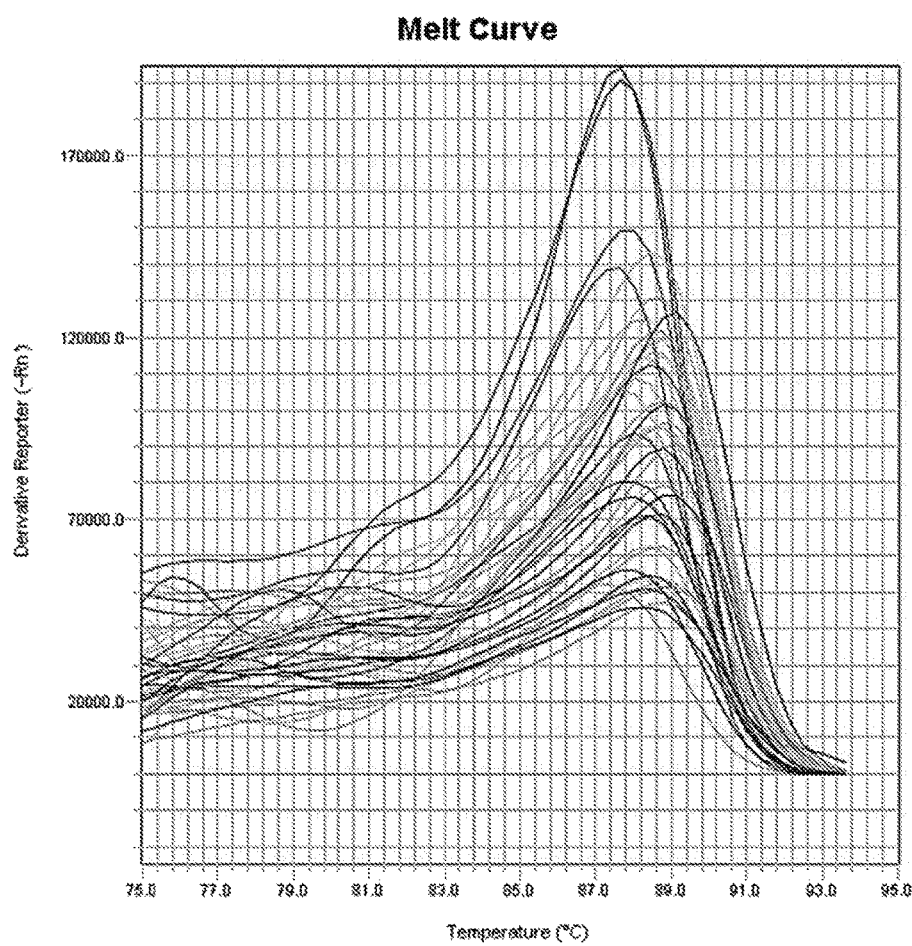
FIGS. 5-8 and 11 describe exemplary melting curve analyses of samples amplified in the device of the present invention by the method of the present invention.
Figure 6:
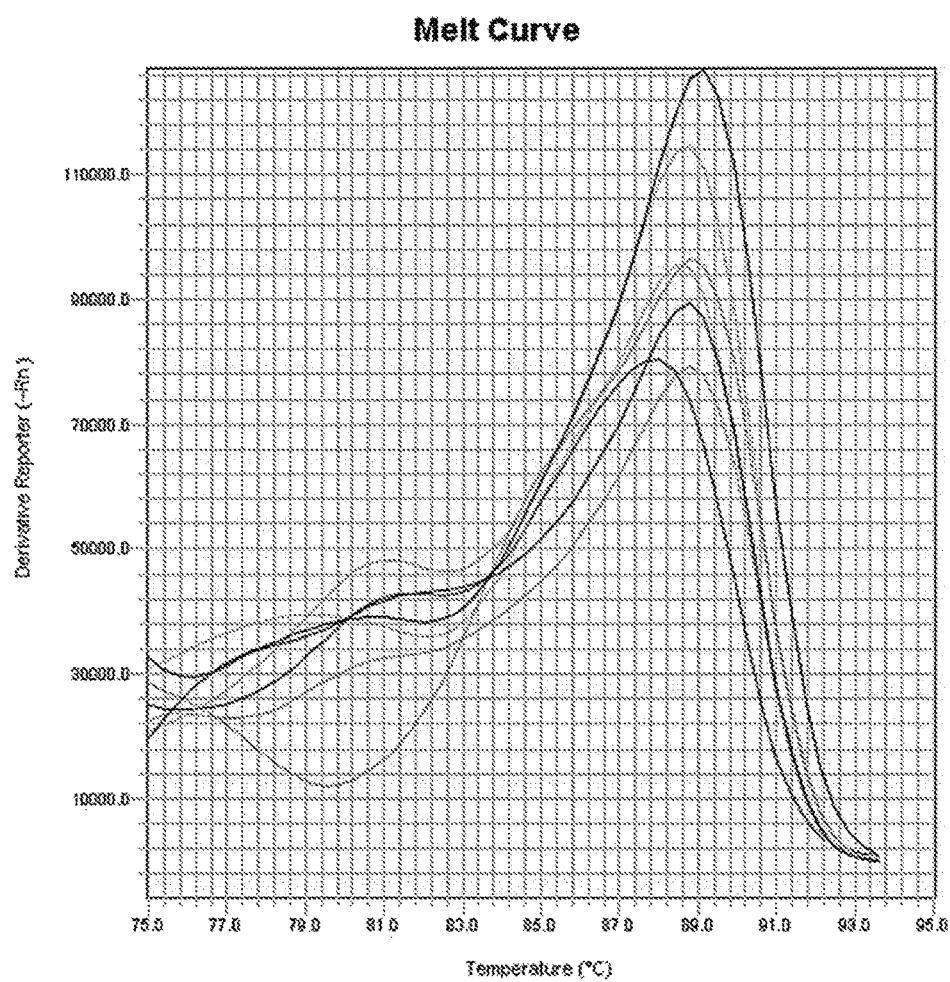
Figure 7:
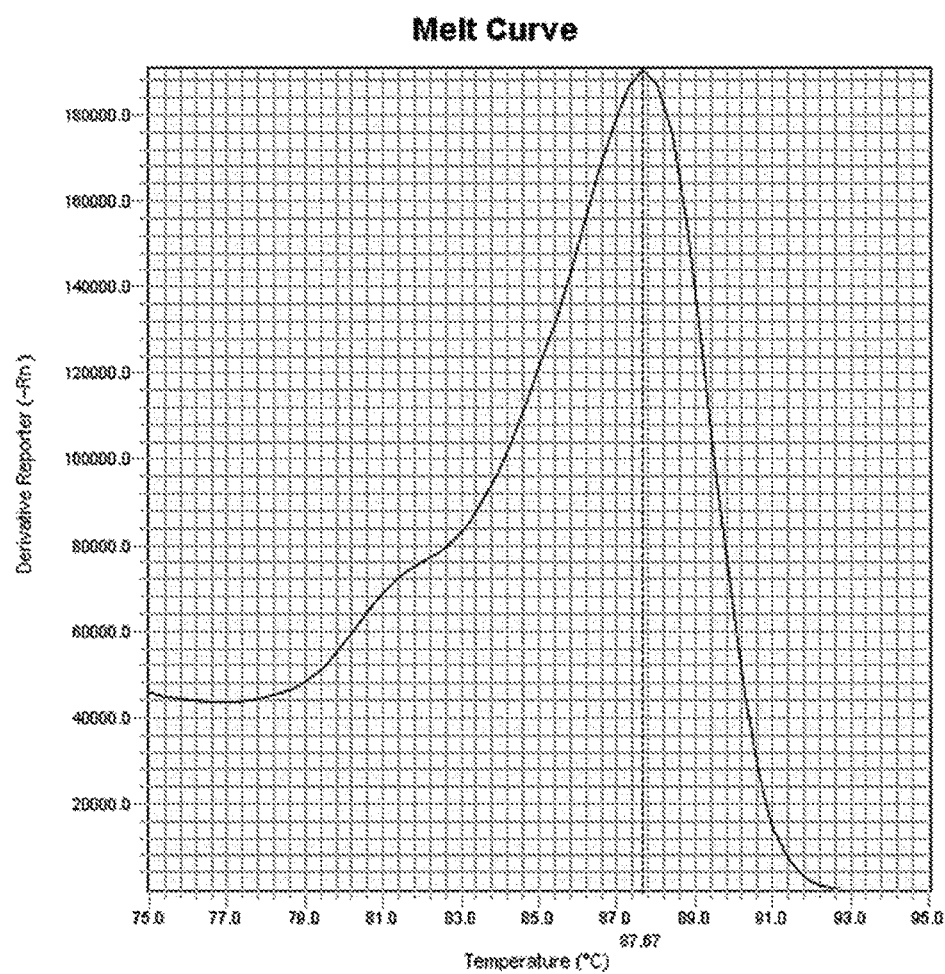

FIG. 4 describes an exemplary device of the present invention comprising: a first heating means (3), wherein the first heating means (3) is a heating block, a sample location (4), a light pipe (1), a second heating means (2), wherein the second heating means (2) is a source of radiation, a light source (5), a camera (8), a dichroic mirror (6), a dichroic mirror (7), wherein at least the dichroic mirrors (6, 7) are inside the light pipe (1), a fluorescence filter (9) and an excitation filter (11).

FIG. 9 describes an exemplary device of the present invention comprising: a first heating means (3), wherein the first heating means (3) is a heating block, a sample location (4), a light pipe (1) of rigid structure, advantageously made of thick metal, a second heating means (2), wherein the second heating means (2) is a source of radiation, a light source (5), a camera (8) and a longpass optical filter (12), wherein the longpass optical filter (12) is inside the light pipe (1) and positioned between the radiation source (2) and the sample location (4).

FIG. 10 describes an exemplary device of the present invention comprising: a first heating means (3), wherein the first heating means (3) is a heating block, a sample location (4), a light pipe (1) of rigid structure, advantageously made of thick metal, wherein said light pipe (1) has at least one opening in its wall, said opening positioned opposite an optical filter (13), a second heating means (2), wherein second heating means (2) is a source of radiation, a light source (5), a camera (8), a longpass optical filter (12), wherein the longpass optical filter (12) is inside the light pipe (1) and positioned between the radiation source (2) and the sample location (4), an optical filter (13), wherein the optical filter (13) is inside the light pipe (1), positioned opposite the opening in the wall of the light pipe (1) and reflects IR radiation and lets visible light pass and an optical filter (14), wherein the optical filter (14) is of same type as the optical filter (13), positioned in the opening in the wall of the light pipe (1) and is configured to increase optical symmetry of the light pipe (1) and to increase uniformity of radiation.

FIGS. 5-8 and 11 describe exemplary melting curve analyses of samples amplified in the device of the present invention:

PCR Amplification Example 1

The use of a light pipe as described herein provides highly efficient and cost-effective way to achieve uniform and simultaneous and ultra-fast distribution of electromagnetic energy to samples and illumination of said samples with light for the purpose of detection. The use of the device (e.g. as described in FIG. 1), light pipe and methods of the present invention demonstrated uniform, simultaneous and ultra-fast thermal cycling of 42 PCR samples of two different sizes. The time necessitated for each PCR cycle consisting of method steps b)-c) was only 3.7 seconds or 7 seconds, which was successfully verified by follow-up analysis of the presence of a specific PCR amplification product (e.g. melting curve analysis). The melting curves show melting of all 42 samples (FIG. 5), a row of 7 samples (FIG. 6) and single melting curve of a single sample (FIG. 7) that were amplified simultaneously in the device described in present invention. PCR was performed using pJET plasmid with cloned LepA gene from mycobacterium smegmatis as a template. Amplified fragment was 126 bp long and contained 58% of GC pairs. Forward primer (FP1-SEQ ID No. 1): tcttgc-cctctttctgcttc, reverse primer (RP1-SEQ ID No. 2): cgcaat-gattctcgagccgatc. The PCR cycle time was 7 seconds and 60 cycles were performed. The starting volume of sample equaled to 0.65 µl and was diluted to 10 µl for the melting curve analysis which was carried out in Applied Biosystems 7500 Fast Real-Time PCR System.

PCR Amplification Example 2

Figure 8:
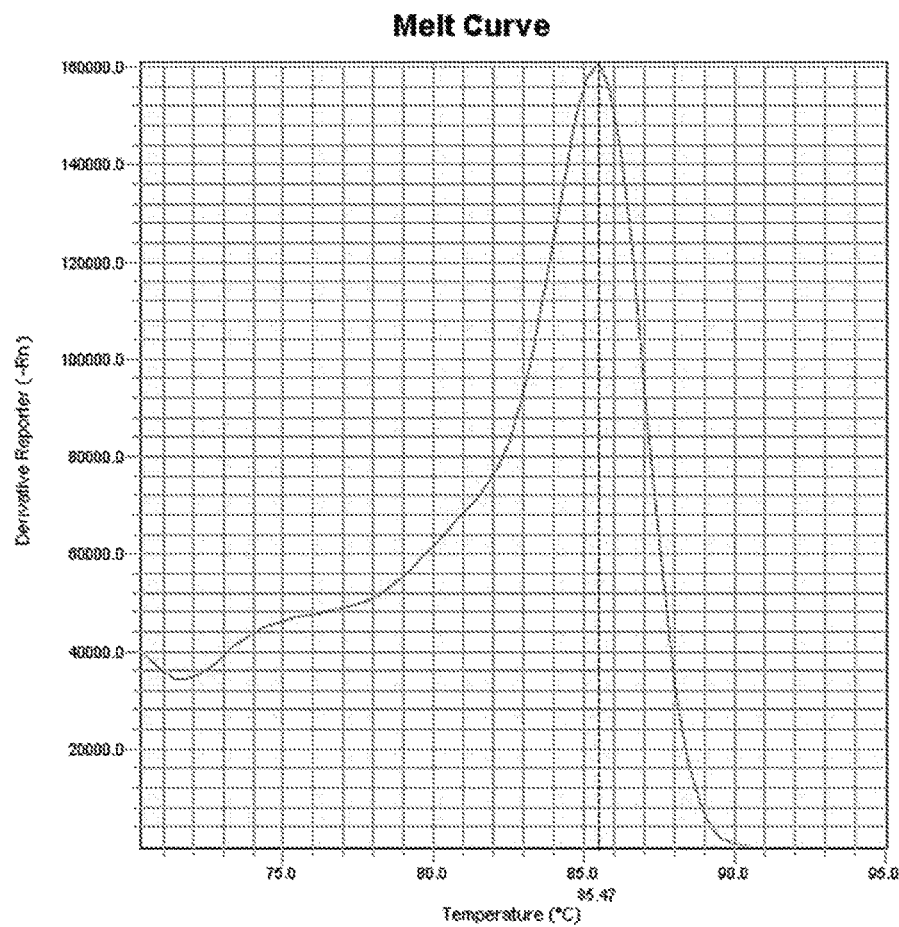

Another melting curve shows melting of the same target amplified with cycle time of 3.7 seconds, the sample volume was 3 µl and the sample was diluted as in the previous example to 10 µl (FIG. 8). Slight change in the melting temperature is caused by changes in buffer composition due to dilution.

PCR Amplification Example 3

Figure 11:
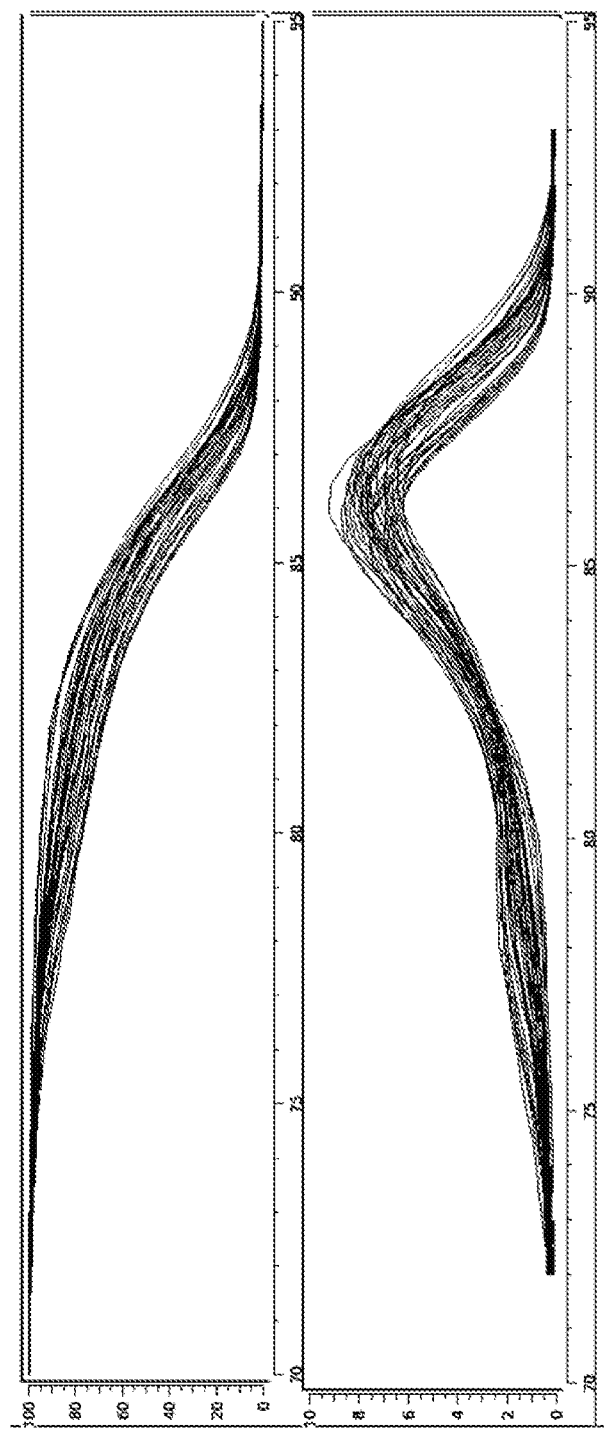

Another PCR amplification experiment was carried in the device according to FIG. 9, which allowed for obtaining melting directly on chip. PCR was performed using pJET plasmid with a cloned human GAPDH gene fragment. Amplified fragment was 125 bp long and contained 53% of GC pairs. Forward primer was (FP2-SEQ ID No. 3): TCTC-CTCTGACTTCAACAGCGAC, reverse primer—(RP2-SEQ ID No. 4): CCCTGTTGCTGTAGCCAAATTC. The heating time was 1.75 seconds (e.g. with halogen on), the cooling time was 5 seconds and 60 cycles were performed. FIG. 11 (y-axis: fluorescence measurement, x-axis: temperature) show melting curve analysis of all 55 samples that were amplified on the chip in the device according to FIG. 9.

All melting curves show specific PCR amplification product with no primer-dimers (e.g. FIGS. 5-8, 11). Therefore, device of the present invention (e.g. as described in FIGS. 1 and 9) produced specific PCR amplification products.

In the sense of the present invention any single embodiment of the present invention mentioned herein can be combined with another single or multiple embodiments of the present invention mentioned herein.

While this invention has been described in terms of several advantageous embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

The invention claimed is:

1. A thermal cycling device comprising:
 a sample location;
 a light source;

a hollow light pipe comprising a first and a second end, wherein inner surfaces of said light pipe are reflective;

a first heater being a contact heat source, wherein said first heater is configured to bring a sample at said sample location to at least about a first temperature;

a second heater being a source of electromagnetic radiation, wherein said second heater is configured to simultaneously bring multiple samples at said sample location to a second temperature by directing the electromagnetic radiation to the first end of the light pipe, and the light pipe is configured to direct said electromagnetic radiation through its second end to the sample location and to homogenize, by means of reflection, a spatial intensity distribution of the electromagnetic radiation; and a camera configured to directly observe emitted fluorescence from the sample location transmitted by the light pipe.

2. The thermal cycling device of claim 1, wherein said camera comprises an objective that only allows the light coming directly from the sample location to pass through.

3. The thermal cycling device of claim 1, wherein said electromagnetic radiation directed to said sample location is configured to simultaneously cause at least 5° C. temperature increase of said multiple samples.

4. The thermal cycling device of claim 1, wherein said second heater is a source of infrared electromagnetic radiation.

5. The thermal cycling device of claim 1, wherein said light pipe is of rigid structure.

6. The thermal cycling device of claim 1, wherein said light pipe is configured to simultaneously illuminate said multiple samples at said sample location with light during thermal cycling by means of reflection.

7. The thermal cycling device of claim 1, wherein said light pipe comprises a chamber that comprises a reflective surface on one side and a semi-reflective surface on the other side.

8. The thermal cycling device of claim 1, further comprising at least one dichroic mirror or a set of dichroic mirrors, within the light pipe as a safety barrier between the camera and the second heater.

9. The thermal cycling device of claim 8, wherein the at least one dichroic mirror is a multiband fluorescence dichroic mirror.

10. The thermal cycling device of claim 1, further comprising at least one fluorescence filter.

11. The thermal cycling device of claim 10, wherein said fluorescence filter is a multiband fluorescence filter.

12. The thermal cycling device of claim 1, further comprising a filter reflecting wavelengths below infrared.

13. The thermal cycling device of claim 11, wherein said fluorescence filter is configured to measure fluorescence intensity changes of a temperature sensitive dye added to said sample.

14. The thermal cycling device of claim 1, wherein said electromagnetic radiation directed to said sample location is configured to simultaneously cause at least 10° C. temperature increase of said multiple samples.

15. The thermal cycling device of claim 1, wherein said electromagnetic radiation directed to said sample location is configured to simultaneously cause at least 15° C. temperature increase of said multiple samples.

16. The thermal cycling device of claim 1, wherein said electromagnetic radiation directed to said sample location is configured to simultaneously cause at least 20° C. temperature increase of said multiple samples.

17. Method for performing thermal cycling using a thermal cycling device comprising a sample location; a light source; a hollow light pipe comprising a first and a second end, wherein inner surfaces of said light pipe are reflective; a first heater being a contact heat source, and configured to bring a sample at said sample location to at least about a first temperature; a second heater being a source of electromagnetic radiation, wherein said second heater is configured to simultaneously bring multiple samples at said sample location to a second temperature by directing the electromagnetic radiation to the first end of the light pipe, and the light pipe is configured to direct said electromagnetic radiation through its second end to the sample location and homogenize, by means of reflection, a spatial intensity distribution of the electromagnetic radiation; and a camera configured to directly observe emitted fluorescence from the sample location transmitted by the light pipe, said method comprising:

directing of said electromagnetic radiation to said sample location using the second heater and using the homogenization of the spatial intensity distribution of electromagnetic radiation;

illuminating said sample location with light during thermal cycling using the light source; and performing real-time fluorescence detection using the camera.

18. A method for uniform and simultaneous amplification of samples with PCR using a thermal cycling device comprising a sample location; a light source; a hollow light pipe comprising a first and a second end, wherein inner surfaces of said light pipe are reflective; a first heater being a contact heat source, wherein said first heater is configured to bring a sample at said sample location to at least about a first temperature; a second heater being a source of electromagnetic radiation, wherein said second heater is configured to simultaneously bring multiple samples at said sample location to a second temperature by directing the electromagnetic radiation to the first end of the light pipe, and the light pipe is configured to direct said electromagnetic radiation through its second end to the sample location and homogenize, by means of reflection, a spatial intensity distribution of the electromagnetic radiation; and a camera configured to directly observe emitted fluorescence from the sample location transmitted by the light pipe, said samples comprising a nucleic acid or a fragment thereof, combined with real time detection of amplified product, said method comprising:

(a) maintaining the temperature of the first heater at a specific temperature, wherein said specific temperature is below or equal to the temperature of the annealing of the PCR primers;

(b) while maintaining said temperature constant, turning on a source of electromagnetic radiation at a constant power for a specified period of time, therein uniformly and simultaneously heating said samples until they reach the temperature of DNA denaturation;

(c) while still maintaining the temperature of the first heater, turning off the source of electromagnetic radiation for a specified period of time, therein cooling said samples; repeating steps (b)-(c) at least 15 times; and (d) after specified period of time turning on the source of fluorescence excitation, therein uniformly and simultaneously exciting said samples, and simultaneously performing detection of emitted fluorescence light using the camera.

19. The method of claim 18, wherein repeating steps (b)-(c) at least 15 times comprises repeating steps (b)-(c) at least 20 times.

20. The method of claim 18, wherein repeating steps (b)-(c) at least 15 times comprises repeating steps (b)-(c) at least 30 times.

21. The method of claim 18, wherein repeating steps (b)-(c) at least 15 times comprises repeating steps (b)-(c) at least 40 times.

22. A method for controlling temperature of samples in real time during thermal cycling, said method comprising: providing the device of claim 13 and keeping the source of fluorescence excitation on or turning it on periodically, while simultaneously reading fluorescence excitation changes caused by change of temperature using the camera during thermal cycling.

23. A thermal cycling device comprising:
  a) a sample location;
  b) a first heater;
  c) a second heater being a source of electromagnetic radiation;
  d) a light source;
  e) a hollow light pipe comprising
   e1) a first light pipe section at least configured to be operated to collect electromagnetic radiation;
   e2) a second light pipe section at least configured to be operated to collect fluorescent excitation and transmit fluorescence emission light; and
   e3) a third light pipe section at least configured to be operated to illuminate said sample location with electromagnetic radiation and fluorescent excitation and to transmit fluorescent emission light to the second light pipe section;
  f) a camera configured to directly observe emitted fluorescence from the sample location transmitted by the light pipe; and
  g) an optical filter configured to reflect visible light and transmit electromagnetic radiation;
  wherein each light pipe section is configured to homogenize, by means of reflection, spatial intensity distribution of light and electromagnetic radiation wherein the first heater is a contact heat source configured to bring a sample at said sample location to at least about a first temperature and said second heater is configured to simultaneously bring multiple samples at said sample location to a second temperature by directing the electromagnetic radiation to the first light pipe section.

24. The thermal cycling device of claim 23, wherein at least one of said first, second or third light pipe sections is made of metal.

25. The thermal cycling device of claim 23, wherein said light pipe is made of metal.

26. The thermal cycling device of claim 23, wherein said third light pipe section is configured to press said sample location to said contact heater.

27. The thermal cycling device of claim 23, wherein said light pipe is configured to press said sample location to said contact heater.

28. The thermal cycling device of claim 23, wherein at least said third light pipe section or light pipe comprises a rigid structure.

* * * * *